(12) United States Patent
Uesaka et al.

(10) Patent No.: US 11,076,862 B2
(45) Date of Patent: Aug. 3, 2021

(54) CLIP UNIT, MEDICAL INSTRUMENT, AND ATTACHING METHOD OF MEDICAL INSTRUMENT

(71) Applicant: OLYMPUS CORPORATION, Hachioji (JP)

(72) Inventors: Kensuke Uesaka, Tokyo (JP); Yasuyuki Fujimoto, Tokyo (JP); Shinya Ansai, Tokyo (JP); Ryu Yorita, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 220 days.

(21) Appl. No.: 16/235,621

(22) Filed: Dec. 28, 2018

(65) Prior Publication Data
US 2020/0205836 A1    Jul. 2, 2020

(51) Int. Cl.
*A61B 17/128*    (2006.01)
*A61B 17/08*    (2006.01)
*A61B 17/10*    (2006.01)
*A61B 17/00*    (2006.01)

(52) U.S. Cl.
CPC ........ *A61B 17/1285* (2013.01); *A61B 17/083* (2013.01); *A61B 17/10* (2013.01); *A61B 2017/0034* (2013.01); *A61B 2017/00367* (2013.01)

(58) Field of Classification Search
CPC . A61B 17/122; A61B 17/1222; A61B 17/128; A61B 17/1285; A61B 17/1227; A61B 17/10; A61B 17/083; A61B 2017/00584; A61B 2017/00367; A61B 2017/0034
See application file for complete search history.

(56) References Cited

U.S. PATENT DOCUMENTS

| 2017/0020531 A1 | 1/2017 | Naveed et al. |
| 2020/0100791 A1* | 4/2020 | Tsuchiya ................ A61B 17/08 |

FOREIGN PATENT DOCUMENTS

WO    WO-2018235402 A1 *  12/2018    ............. A61B 17/10

* cited by examiner

*Primary Examiner* — Ashley L Fishback
(74) *Attorney, Agent, or Firm* — Oliff PLC

(57) ABSTRACT

A medical instrument has a capsule; an arm member disposed to protrude from the capsule; an operation wire connected to the arm member; a sheath configured to accommodate the operation wire; and a link configured to connect the sheath with the capsule, wherein the link has an engaging portion including a first surface intersecting with the longitudinal axis; and an engaged portion movable to an opposite position opposite to the first surface and a position spaced away from the first surface in spite of a relative position of the capsule with respect to the sheath, and configured to restrict a separation of the capsule with respect to the sheath when the engaged portion is disposed at the opposition position to contact the first surface, and wherein the capsule is rotatable in response to a rotation force from the sheath when the engaged portion is disposed at the opposition position.

15 Claims, 27 Drawing Sheets

FIG. 7
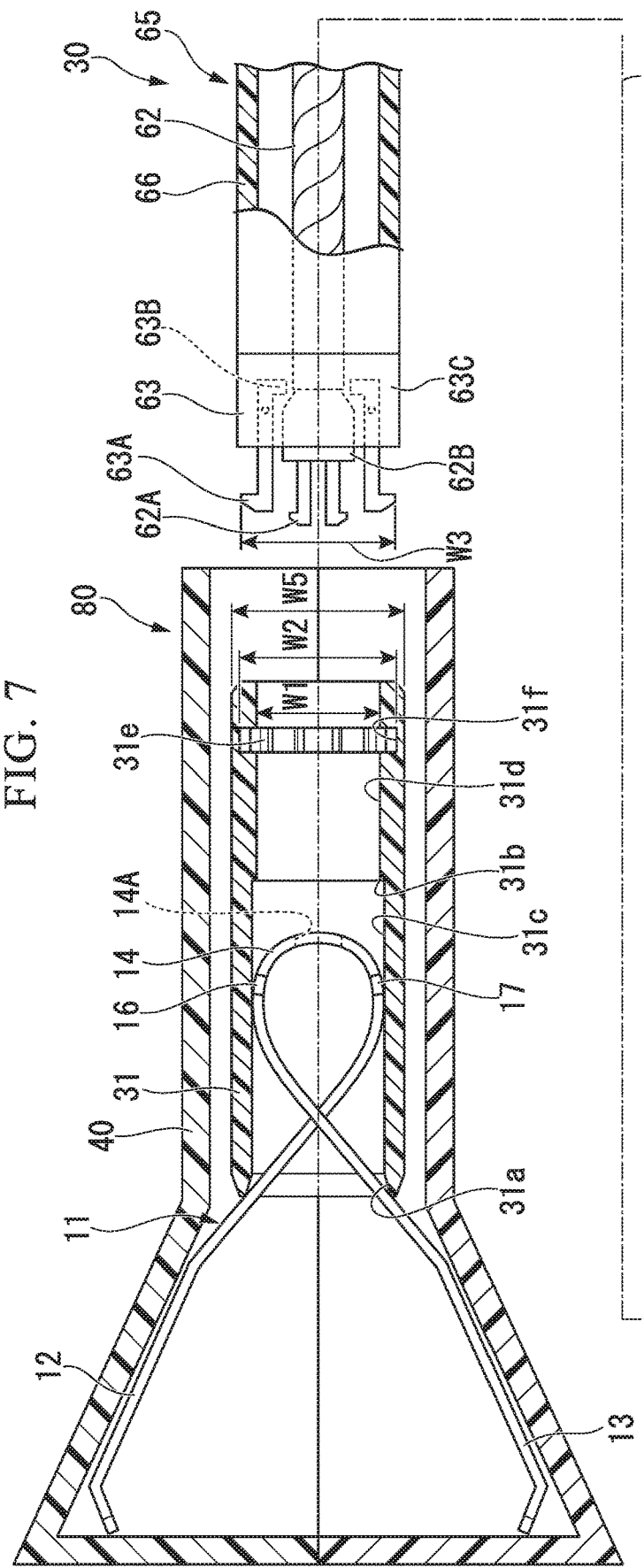
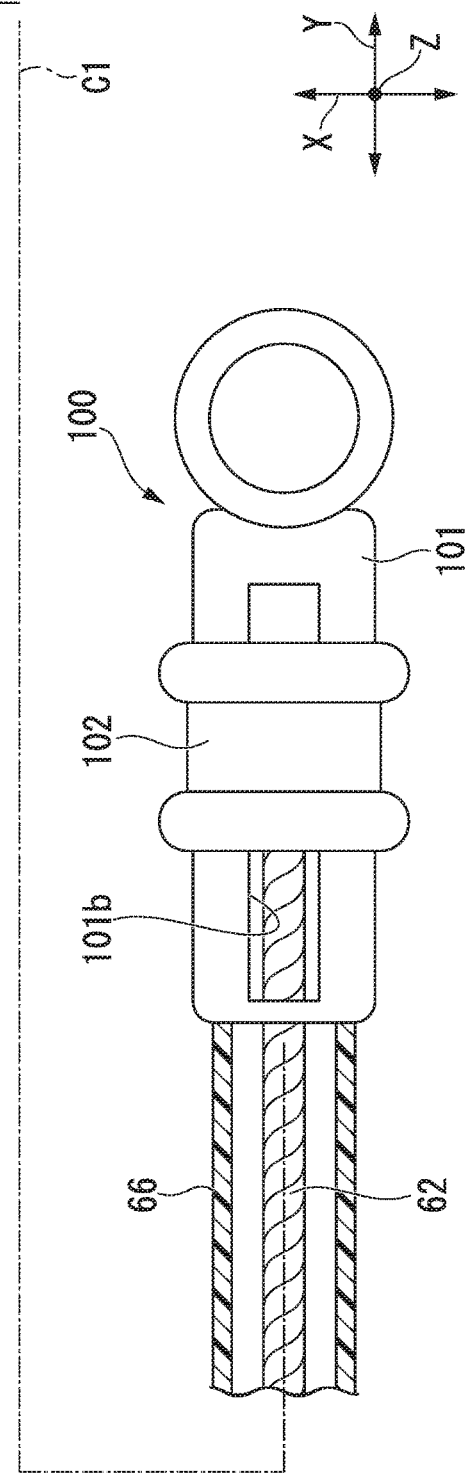

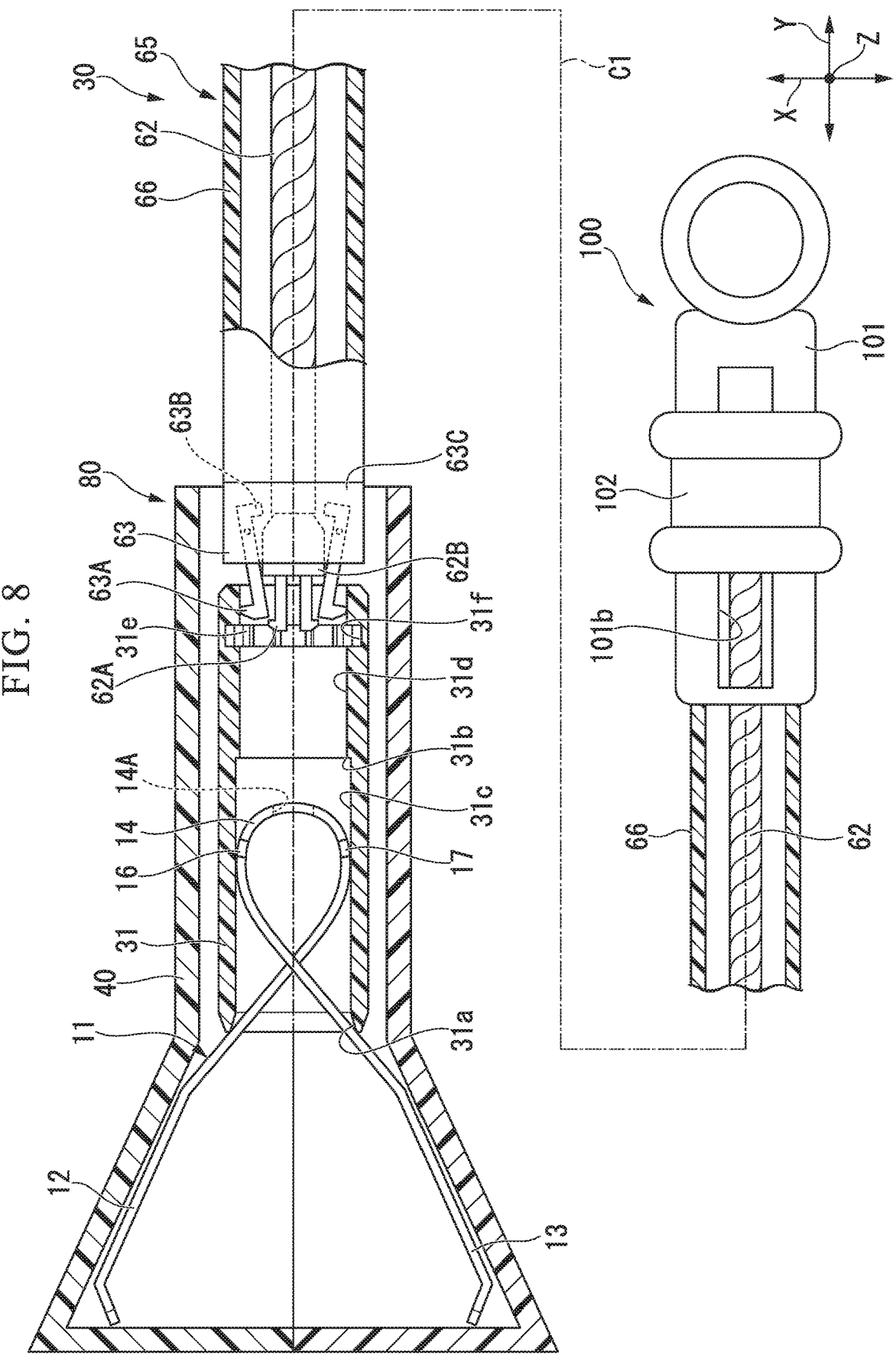

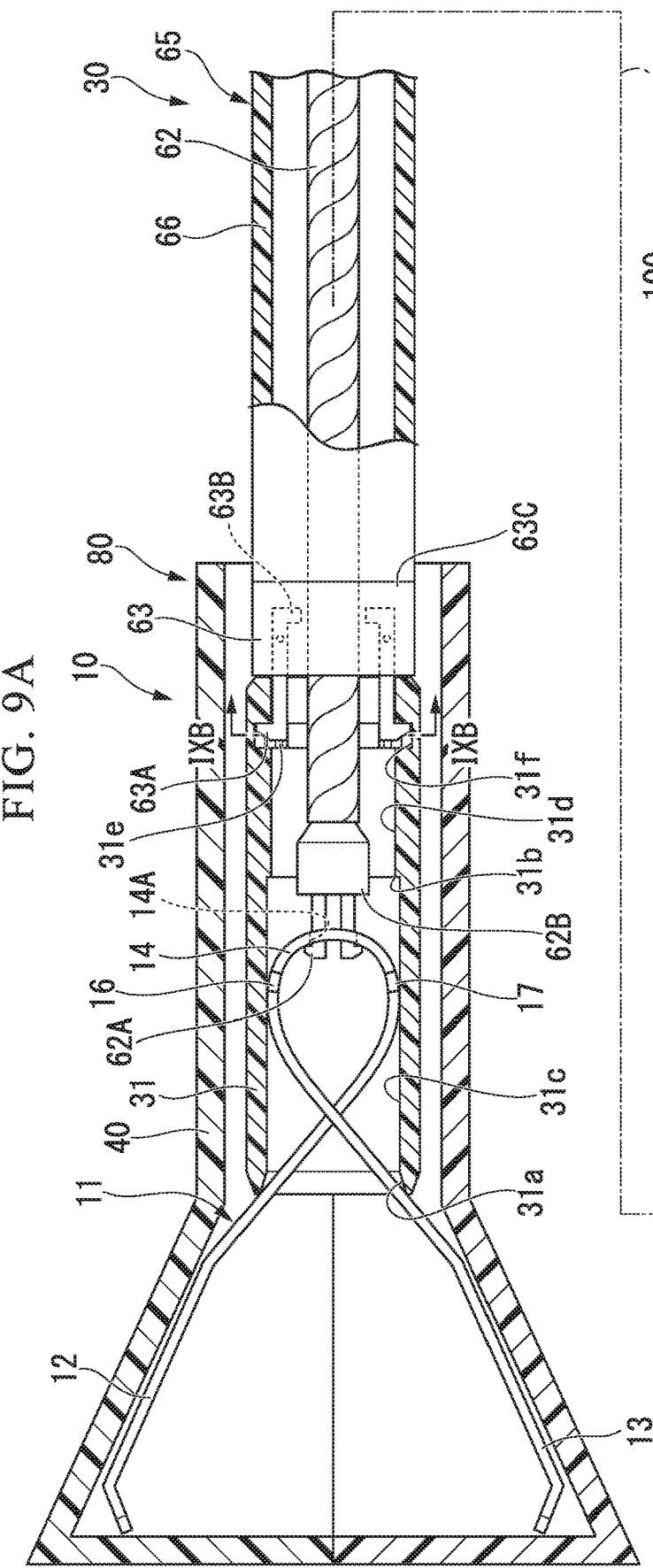
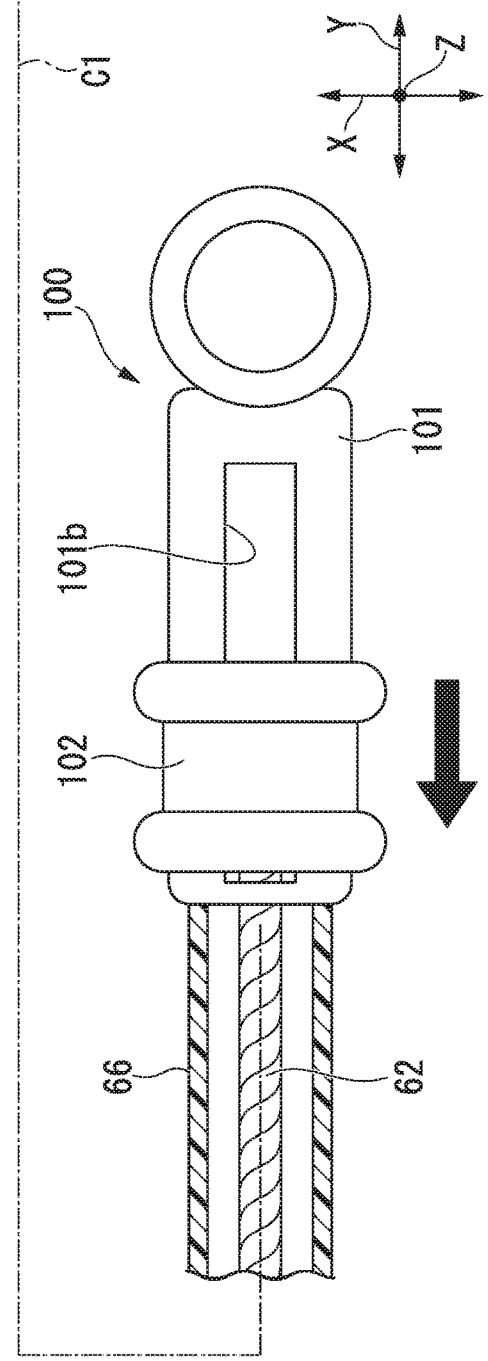
FIG. 9A

FIG. 13
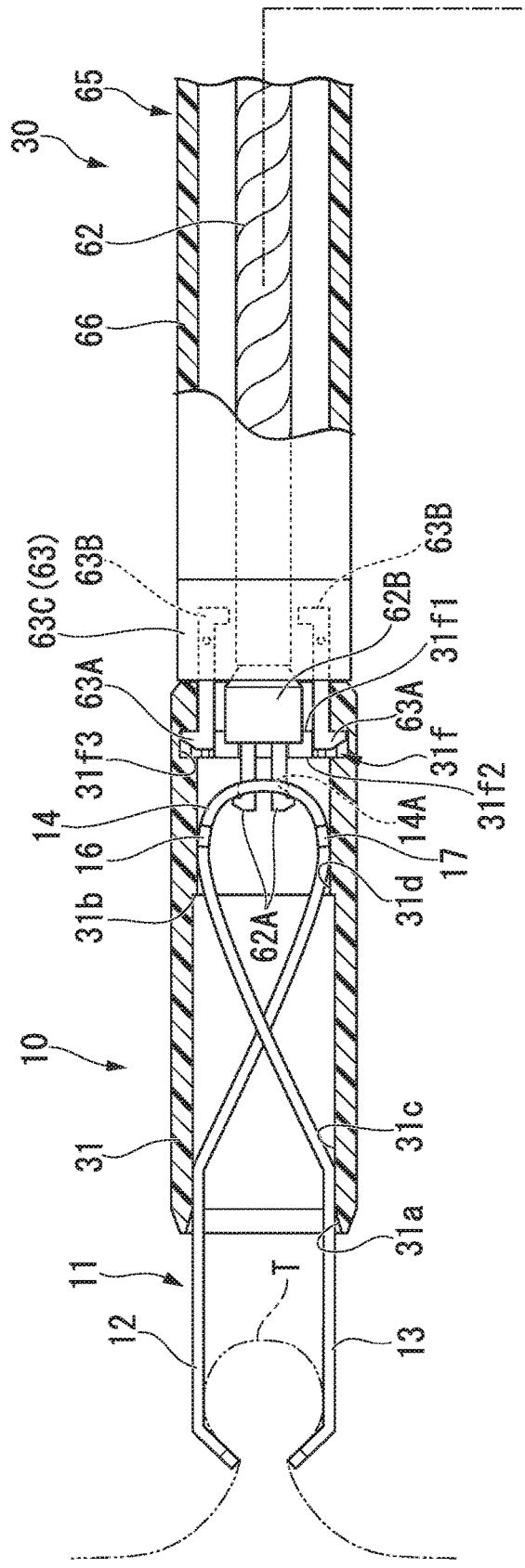
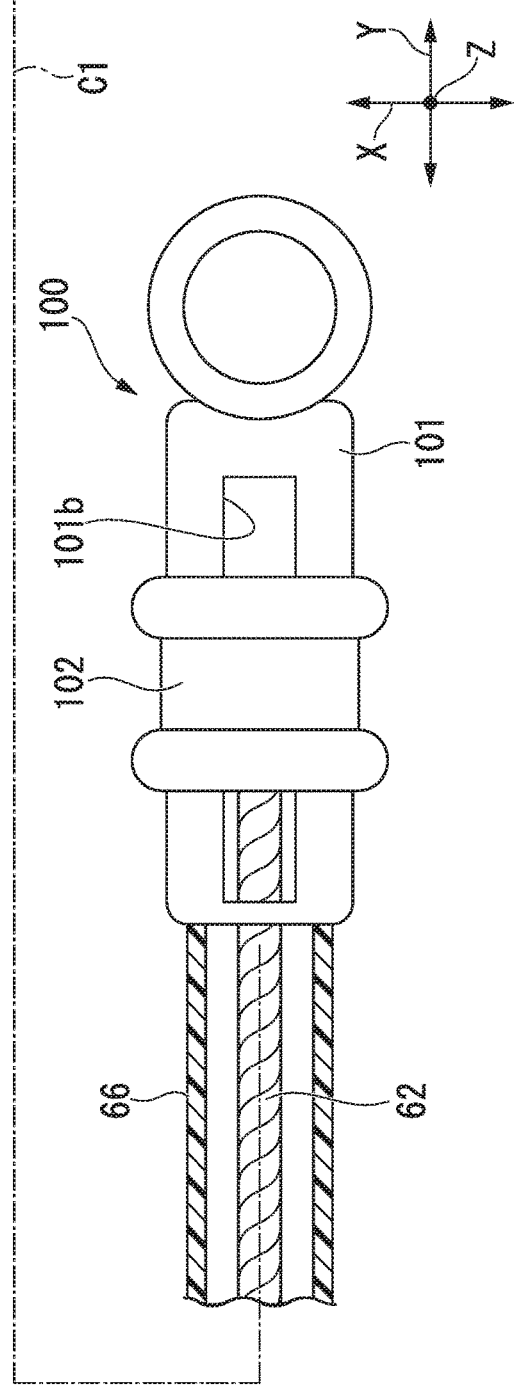

US 11,076,862 B2

CLIP UNIT, MEDICAL INSTRUMENT, AND ATTACHING METHOD OF MEDICAL INSTRUMENT

TECHNICAL FIELD

The present invention relates to a clip unit configured to treat target issues in the body, a medical instrument (more specifically, a ligation device for ligating the tissues), and an attaching method of the medical instrument.

BACKGROUND ART

Conventionally, a reloadable ligation device is known as disclosed in U.S. Patent Application Publication No. 2017/0020531 A1. The reloadable ligation device is configured to ligate openings formed on the target tissues in the body and blood vessels by being introduced into the body of a patient through a channel of an endoscope.

The ligation device disclosed in U.S. Patent Application Publication No. 2017/0020531 A1 is configured by coupling a clip accommodated in a clip case and an applicator configured to operate the clip. The clip is configured to have a pair of arms inserted from the distal end side of a capsule.

In the ligation device disclosed in U.S. Patent Application Publication No. 2017/0020531 A1, when the clip is accommodated in the clip case, an operator firstly inserts a large-diameter portion provided at a distal end of the applicator to a slit formed in the capsule of the clip and then fits a pair of coupling fingers provided at the distal end of the applicator into a pair of coupling windows formed in the capsule of the clip respectively so as to couple the clip with the applicator. However, during the process, the operator has to match phases of the pair of coupling fingers provided at the distal end of the applicator and the pair of coupling windows formed in the capsule of the clip in a circumferential direction thereof.

SUMMARY OF INVENTION

According to a first embodiment of the present invention, a medical instrument is configured to have a capsule formed in a cylindrical shape and has a longitudinal axis; an arm member disposed to protrude from the capsule and configured to be rotatable together with the capsule about the longitudinal axis; an operation wire connected to the arm member, the operation wire being separatable from the arm member; a sheath configured to accommodate the operation wire; and a link configured to connect the sheath with the capsule, the sheath and the capsule being separatable from each other, wherein the link has: an engaging portion including a first surface intersecting with the longitudinal axis; and an engaged portion configured to protrude in an intersection direction with respect to the longitudinal axis, the engaged portion being movable to an opposite position opposite to the first surface and a position spaced away from the first surface in the intersection direction in spite of a relative position of the capsule with respect to the sheath in a circumferential direction about the longitudinal axis, and the engaged portion being configured to restrict a separation of the capsule with respect to the sheath when the engaged portion is disposed at the opposition position to contact the first surface, and wherein the capsule is rotatable about the longitudinal axis in response to a rotation force about the longitudinal axis from the sheath when the engaged portion is disposed at the opposition position.

According to a second aspect of the present invention, in the medical instrument according to the first aspect, the first surface may extend over a whole circumference about the longitudinal axis.

According to a third aspect of the present invention, in the medical instrument according to the first aspect, the arm member may be connected to the operation wire and freely rotatable about the longitudinal axis, and the arm member, the capsule, and the sheath may be configured to rotate about the longitudinal axis with respect to the operation wire.

According to a fourth aspect of the present invention, in the medical instrument according to the first aspect, the engaged portion may be provided in the sheath and the engaging portion may be formed on an inner peripheral surface or an outer peripheral surface of the capsule.

According to a fifth aspect of the present invention, in the medical instrument according to the first aspect, the engaged portion may be provided in the capsule and the engaging portion is formed on an inner peripheral surface or an outer peripheral surface of the sheath.

According to a sixth aspect of the present invention, in the medical instrument according to the first aspect, the link may be configured to transmit the rotation force about the longitudinal axis from the sheath to the capsule due to an engagement of the engaging portion and the engaged portion.

According to a seventh aspect of the present invention, in the medical instrument according to the sixth aspect, the engaging portion may have a second surface which faces a direction different from that of the first surface, and the second surface may be configured to transmit the rotation force of the sheath to the capsule by contacting the engaged portion when the capsule rotates about the longitudinal axis with respect to the sheath and the engaged portion is positioned at the opposition position.

According to an eighth aspect of the present invention, in the medical instrument according to the seventh aspect, the second surface may be disposed at a deeper side of the groove than the first surface in the whole circumference about the longitudinal axis.

According to a ninth aspect of the present invention, in the medical instrument according to the seventh aspect, the second surface may be disposed at a position opposite to the engaged portion in the circumferential direction about the longitudinal axis when the engaged portion is disposed at the opposition position, and the second surface may be configured to transmit the rotation force of the sheath to the capsule when the second surface contacts with the engaged portion due to the rotation of the capsule about the longitudinal axis with respect to the sheath.

According to a tenth aspect of the present invention, in the medical instrument according to the seventh aspect, the second surface may contact the engaged portion when the engaged portion is disposed at the opposition position, and the second surface may be configured to transmit the rotation force of the sheath to the capsule by a friction force generated between the second surface and the engaged portion when the capsule rotates about the longitudinal axis with respect to the sheath.

According to an eleventh aspect of the present invention, in the medical instrument according to the seventh aspect, the first surface may contact the engaged portion when the engaged portion is disposed at the opposition position, and the first surface may be configured to transmit the rotation force of the sheath to the capsule by a friction force generated between the second surface and the engaged portion when the capsule rotates about the longitudinal axis with respect to the sheath.

According to a twelfth aspect of the present invention, in the medical instrument according to the first aspect, the capsule may have the engaging portion provided at a surface of the capsule, the sheath may have the engaged portion provided at a surface of the sheath, the engaged portion being engaged with the engaging portion when the engaged portion is disposed at the opposition position, and the rotation force of the sheath may be transmitted to the capsule due to an engagement of the engaging portion and the engaged portion.

According to a thirteenth aspect of the present invention, in the medical instrument according to the twelfth aspect, the engaging portion and the engaged portion may be engaged with each other due to a concave structure with a convex structure which can be coupled with each other.

According to a fourteenth aspect of the present invention, a clip unit connected to an applicator, the clip unit and the applicator being separatable from each other, and the applicator having an operation wire operated by an operator, a sheath configured to accommodate the operation wire, and an engaged portion protruding in an intersection direction intersecting with a central axis of the sheath, has: a capsule formed in a cylindrical shape and has a longitudinal axis, the capsule being connected to the sheath and separatable from the sheath; and an arm member disposed to protrude from the capsule, the arm member being connected to the operation wire and separatable from the operation wire, wherein the arm member is configured to be integrally rotatable with the capsule about the longitudinal axis, wherein the capsule has an engaging portion with a first surface intersecting with the longitudinal axis, wherein the first surface can face the engaged portion in spite of a relative position of the capsule with respect to the sheath in a circumferential direction about the longitudinal axis, and the first surface can restrict a separation of the capsule from the sheath by contacting the engaged portion in an opposition state in which the first surface faces the engaged portion, and wherein the capsule is rotatable about the longitudinal axis in response to a rotation force about the longitudinal axis from the sheath when the first surface is in the opposition state.

According to a fifteenth aspect of the present invention, an attaching method of a medical instrument having a capsule and a sheath for attaching the capsule to the sheath, wherein the medical instrument has: the capsule formed in a cylindrical shape and has a longitudinal axis; an arm member disposed to protrude from the capsule and configured to be internally rotatable with the capsule about the longitudinal axis; an operation wire connected to the arm member, the operation wire being separatable from the arm member; a sheath configured to accommodate the operation wire; and a link configured to connect the sheath with the capsule, the sheath and the capsule being separatable from each other, wherein the link has: an engaging portion including a first surface intersecting with the longitudinal axis; an engaged portion configured to protrude in an intersection direction with respect to the longitudinal axis, the engaged portion being movable to an opposite position opposite to the first surface and a position spaced away from the first surface in the intersection direction in spite of a relative position of the capsule with respect to the sheath in a circumferential direction about the longitudinal axis, and the engaged portion being configured to restrict a separation of the capsule with respect to the sheath when the engaged portion is disposed at the opposition position to contact the first surface; and an elastic portion configured to generate an elastic force so as to bias the engaged portion toward the side of the opposition position in the intersection direction, and wherein the capsule is rotatable about the longitudinal axis in response to a rotation force about the longitudinal axis from the sheath when the engaged portion is disposed at the opposition position, the attaching method includes: a step of moving the engaged portion in the intersection direction against the elastic force of the elastic portion; a step of moving the engaged portion in the longitudinal direction so as to dispose the engaged portion at a position more distal than that of the first surface; and a step of moving the engaged portion to the opposition position by the elastic force of the elastic portion at an arbitrary position about the longitudinal axis.

BRIEF DESCRIPTION OF DRAWINGS

FIG. 7 is a view showing an operation for attaching the clip unit to the applicator according to the present embodiment.

FIG. 8 is a view showing the operation for attaching the clip unit to the applicator according to the present embodiment.

FIG. 9A is a view showing the operation for attaching the clip unit to the applicator according to the present embodiment.

FIG. 13 is a view showing an operation for treating a target issues using the medical instrument according to the present embodiment.

DESCRIPTION OF EMBODIMENT

A first embodiment of the present invention will be described with reference to FIG. 1 to FIG. 16. A medical instrument 1 according to the present embodiment is used by being inserted into the body of a patient through a channel formed in an endoscope not shown. More specifically, the medical instrument 1 according to the present embodiment is a ligation instrument configured to ligating the target tissues inside the body.

In this description, a proximal end side is defined as a side at which an operation portion of an endoscope is disposed, wherein the operation portion is configured for a user to operate the endoscope, and a distal end side is defined as a side at which a distal end of the endoscope that is inserted into the body is disposed. More specifically, the proximal end side of the medical instrument 1 according to the present embodiment is defined as the side at which the operation portion of the endoscope is disposed when the medical instrument 1 is inserted into the channel formed on the endoscope. The distal end side of the medical instrument 1 is defined as the side at which the distal end portion of the endoscope is disposed when the medical instrument 1 is inserted into the channel formed on the endoscope.

(Configuration of Clip Unit)

Figure 11:
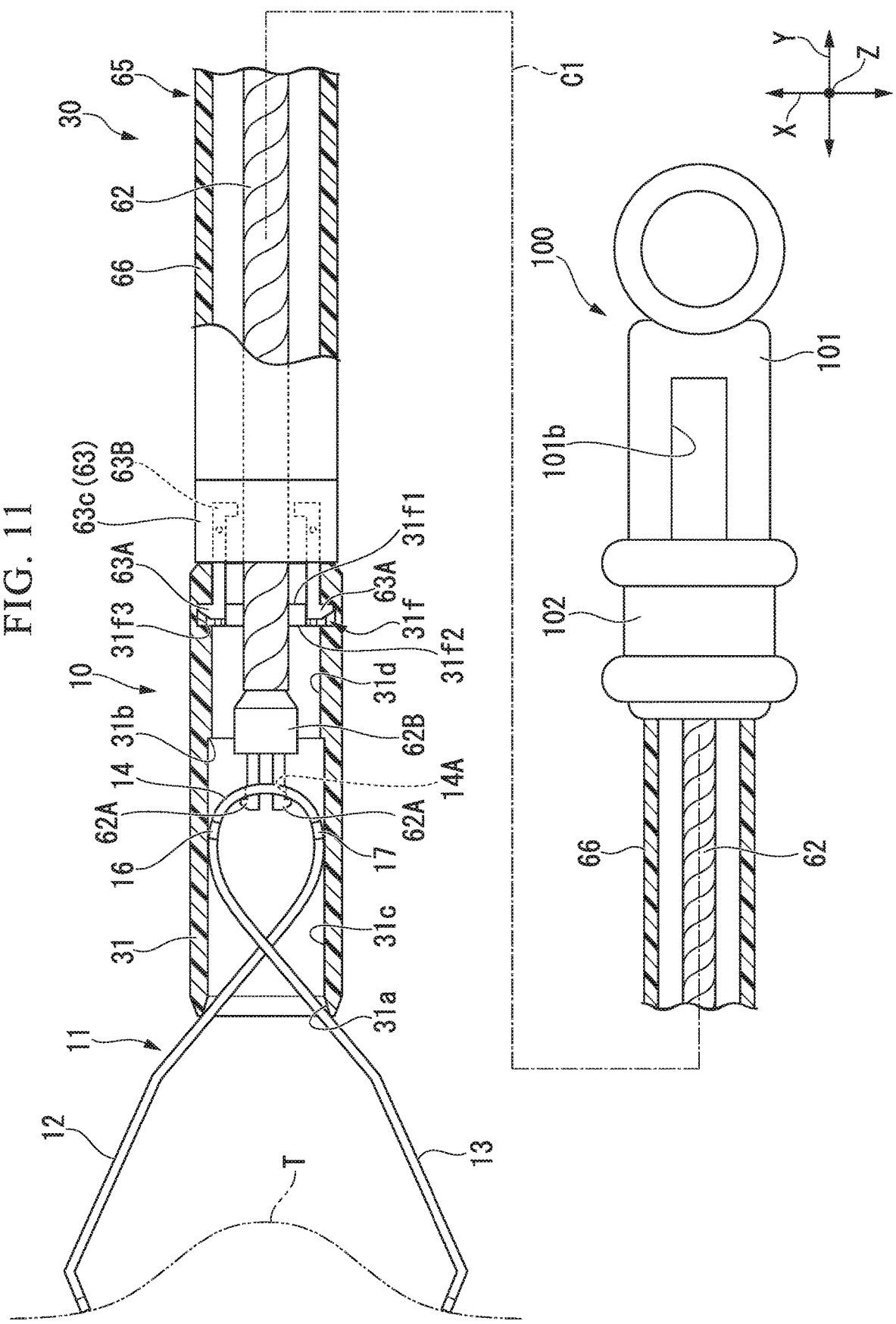
FIG. 11 is a view showing an operation for treating a target issues using the medical instrument according to the present embodiment.

The medical instrument 1 according to the present embodiment has a clip unit (clip) 10 provided at the distal end side and an applicator 30 configured to be attachable to the clip 10 (see FIG. 11). Next, the clip 10 according to the present embodiment will be described with reference to FIG. 1 to FIG. 5.

Figure 1:
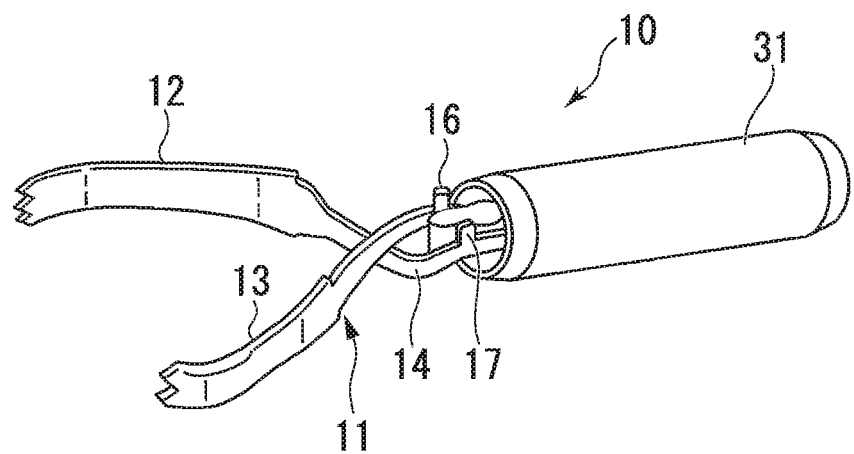
FIG. 1 is a perspective view schematically showing a configuration of a clip unit according to a first embodiment of the present invention.
Figure 2:
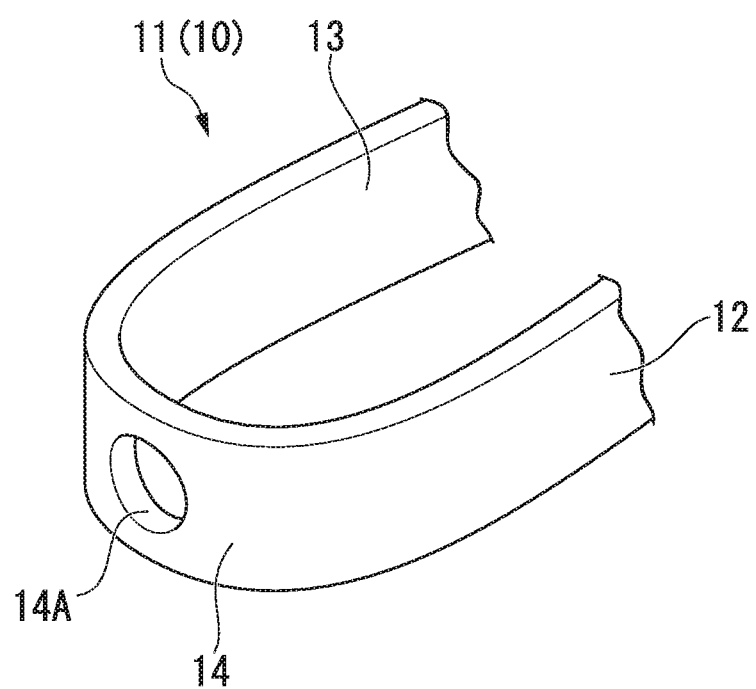
FIG. 2 is a perspective view schematically showing a configuration of a part at a proximal end side of an arm member of the clip unit according to the present embodiment.
Figure 3:
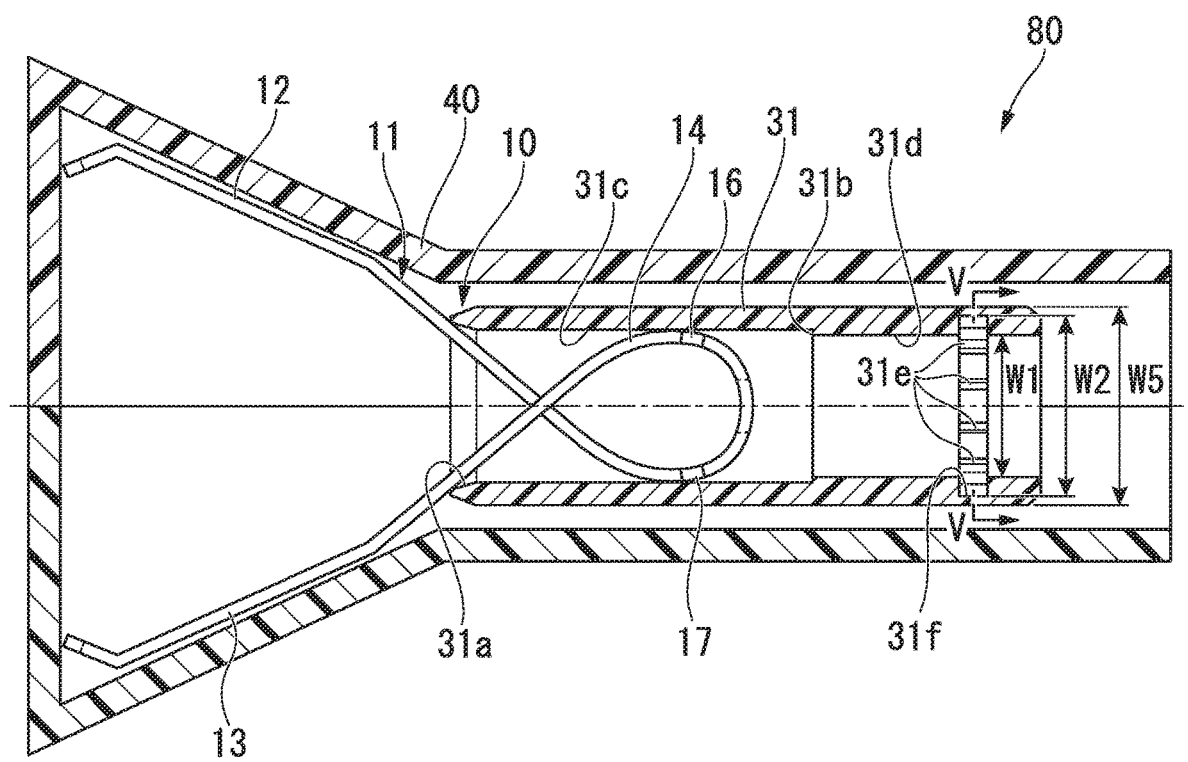
FIG. 3 is a partial cross-sectional view in a lateral view schematically showing the configuration of the clip unit according to the present embodiment.
Figure 4:
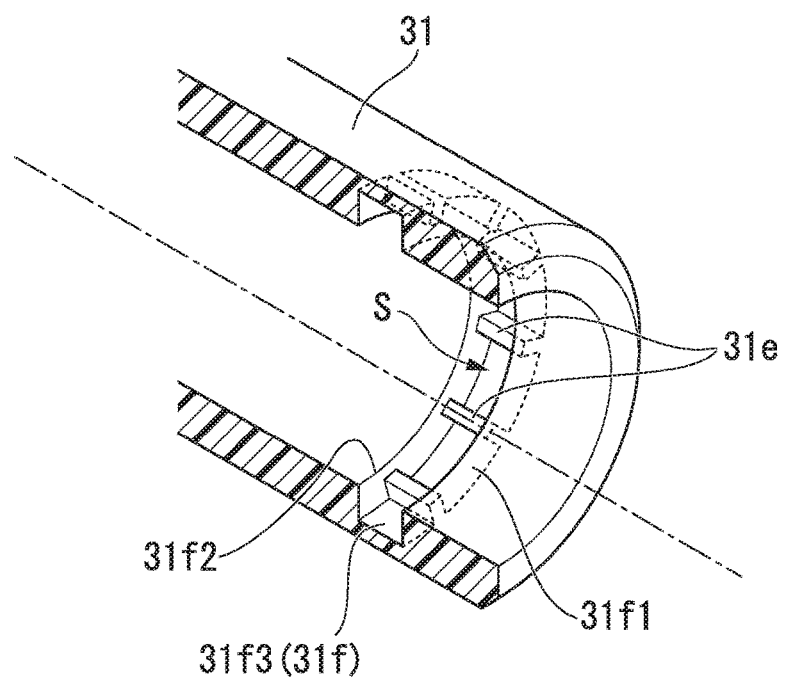
FIG. 4 is a partial cross-sectional view schematically showing the configuration of part of the clip unit according to the present embodiment.
Figure 5:
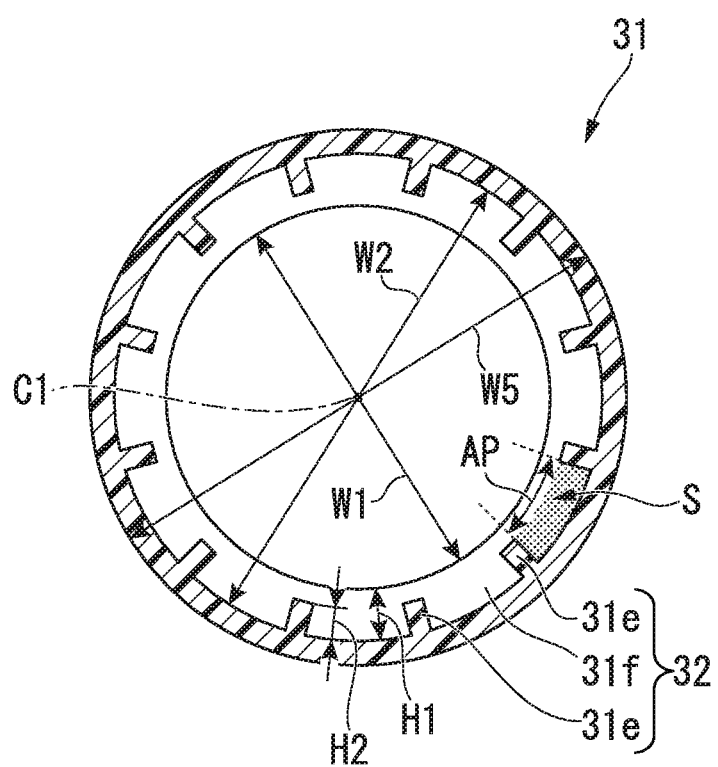
FIG. 5 is a cross-sectional view along the line V-V in FIG. 3.

FIG. 1 is a perspective view schematically showing a configuration of the clip 10 according to the present embodiment. FIG. 2 is a perspective view schematically showing a configuration of the proximal end side of an arm member 11 of the clip 10. FIG. 3 is a partial cross-sectional view in a lateral view schematically showing a configuration of a pressing tube (capsule) 30 of the clip 10. FIG. 4 is a partial cross-sectional view showing a configuration of an engaging portion 32 formed by cutting and removing part of the pressing tube 31 in an outward radial direction from an inner circumferential surface of the pressing tube 31. FIG. 5 is a cross-sectional view showing the configuration of the engaging portion 32 formed by cutting along the V-V line in FIG. 3.

As shown in FIG. 1, the clip 10 is configured to have the arm member 11 and the pressing tube (capsule) 31. The arm member 11 has a first arm 12, a second arm 13, and an intermediate portion 14. The first arm 12 and the second arm 13 extend from the proximal end side toward the distal end side while facing each other. The arm member 11 is configured by crossing the first arm 12 and the second arm 13 with each other. As shown in FIG. 3, the first arm 12 and the second arm 13 may be arranged in linear symmetrical positions with a longitudinal axis (axis C1) of the pressing tube 31 as the line symmetry center.

In the present embodiment, for convenience of description, the axis C1 will be regarded as the longitudinal axis of the pressing tube 31, a longitudinal axis of the arm member 11, a longitudinal axis of an insertion portion, and a longitudinal axis of an operation portion 10 which will be described later.

The intermediate portion 14 is positioned between the proximal end portion of the first arm 12 and the proximal end portion of the second arm 13. In other words, the intermediate portion 14 is defined as a part of the arm member 11 which is more proximal than a crossing section at which the first arm 12 and the second arm 13 cross with each other. As shown in FIG. 2, an insertion port 14A is formed in the intermediate portion 14, wherein the insertion port 14A has a width such that a pair of hooks 62A disposed at a distal end of an operation wire 62 described below can enter at the insertion port 14A. According to the present embodiment, the insertion port 14A only has to be formed with the width such that the pair of hooks 62A described below can enter at the insertion port 14A, and the shape of the insertion port 14A is not limited thereto.

The first arm 12 and the second arm 13 of the arm member 11 extend from the proximal end side toward the distal end side and the first arm 12 and the second arm 13 are disposed to face each other. The first arm 12 and the second arm 13 have an elastic restoring force respectively such that in a natural state in which neither an external force is applied to the arm member 11, the first arm 12 and the second arm 13 separate from each other and a distance between the first arm 12 and the second arm 13 gradually increases in a direction from the proximal end side toward the distal end side. The arm member 11 is biased to the direction so as to have a tendency to move distally due to the elastic restoring force of the first arm 12 and the second arm 13.

In the intermediate portion 14 of the arm member 11, a pair of protrusions 16, 17 are formed to protrude in directions orthogonal to the longitudinal direction (the direction along the axis C1) along which the first arm 12 and the second arm 13 extend. The pair of protrusions 16, 17 may be formed in linear symmetrical positions with respect to the longitudinal axis of the arm member 11. The pair of protrusions 16, 17 formed in the intermediate portion 14 of the arm member 11 can limit a movement of the arm member 11 relative to the pressing tube 31 by being anchored in the inner circumferential surface of a small-diameter portion 31b of the pressing tube 31 described below.

The arm member 11, for example, can be formed by firstly bending a metal material such as a stainless leaf spring to form the first arm 12 and the second arm 13, and then making the first arm 12 and the second arm 13 to cross with each other. The arm member 11 has the configuration described above so as to be slidable along the inner circumferential surface of the pressing tube 31 while being retracted into the pressing tube 31.

The pressing tube (capsule) 31 is formed in a tubular shape to have an inner diameter such that the proximal end portion of the arm member 11 can enter. In other words, a lumen is formed in the pressing tube 31 for the first arm 12 and the second arm 13 of the arm member 11 to enter. The lumen formed in the pressing tube 31 is also formed for the pair of hooks 62A disposed at the distal end side of the operation wire 62 described below to enter. As shown in FIG. 3, a tapered surface 31a is formed over the whole circumference of the inner wall at the distal end portion of the pressing tube 31. The tapered surface 31a is formed to have a gradually increased diameter toward the distal end side. In the present embodiment, for example, the pressing tube 31 may be integrally formed from a material such as a 64 titanium alloy (Ti-6AL-4V) or a cobalt chromium alloy and the like.

In the pressing tube 31, a step portion 31b is formed over the whole inner circumferential surface of the pressing tube 31 to protrude inwardly in the radial direction. The pressing tube 31 is formed to have a large-diameter portion 31c more distal than the step portion 31b and a small-diameter portion 31d more proximal than the step portion 31b. In the present embodiment, the width of part of the arm member 11 at which the pair of protrusions 16, 17 are formed may be determined to be smaller than the diameter of the large-diameter portion 31c of the pressing tube 31 and larger than the diameter of the small-diameter portion 31d of the pressing tube 31. Accordingly, as described below, the arm member 11 is freely slidable along the inner circumferential surface of the pressing tube 31 in the large-diameter portion 31c more distal than the step portion 31b of the pressing tube 31. On the other hand, in the small-diameter portion 31d more proximal than the step portion 31b of the pressing tube 31, the arm member 11 can be moved proximally along the inner circumferential surface of the pressing tube 31; however, since the pair of protrusions 16, 17 bite into the inner circumferential surface of the small-diameter portion 32d of the pressing tube 31, the arm member 11 cannot be moved distally relative to the pressing tube 31. In other words, when the arm member 11 is retracted into the pressing tube 31 so as to be at a position more proximal than the step portion 31b, the movement of the arm member 11 toward the distal end side relative to the pressing tube 31 is limited.

In the present embodiment, as shown in FIG. 3 and FIG. 4, in the small-diameter portion 31d more proximal than the step portion 31b in the pressing tube 31, an inner-groove portion 31f is formed by cutting and removing part of the pressing tube 31 over the whole circumference on the inner circumferential surface of the pressing tube 31. In other words, at the inner-groove portion 31f formed in the small-diameter portion 31d of the pressing tube 31, a thickness of the pressing tube 31 in the radial direction becomes thinner than other part of the pressing tube 31.

In the present embodiment, a plurality of ribs 31e are formed to extend along the longitudinal direction (direction along the axis C1) of the pressing tube 31 between a proximal wall (first surface) 31f1 and a distal wall (second surface) 31f2 of the inner-groove portion 31f formed in the small-diameter portion 31d of the pressing tube 31. In other words, the plurality of ribs 31e are formed to inwardly protrude from the inner circumferential surface of the inner-groove portion 31f of the pressing tube 31 in the radial direction.

As shown in FIG. 3 and FIG. 4, in the longitudinal direction of the pressing tube 31, the plurality of ribs 31e are formed to connect the proximal wall 31f1 and the distal wall 31f2 of the inner-groove portion 31f. Accordingly, the plurality of ribs 31e have the same width as the width of the inner-groove portion 31f in the longitudinal direction of the pressing tube 31. On the other hand, as shown in FIG. 5, in the radial direction of the pressing tube 31, a height H2 of the plurality of fibs 31e is smaller than a depth H1 of the inner-groove portion 31f. That is, the plurality of ribs 31e are formed to protrude inwardly from the inner circumferential surface 31/3 of the inner-groove portion 31f of the pressing tube 31 in the radial direction of the pressing tube 31; however, the plurality of ribs 31e do not protrude inwardly beyond the small-diameter portion 31d of the pressing tube 31 in the radial direction. As shown in FIG. 3 and FIG. 5, in the pressing tube 31 according to the present embodiment, the small-diameter portion 31d has a width W1, the inner-groove portion 31f has a width W2, and the pressing tube 31 has an outer diameter W5.

As shown in FIG. 4 and FIG. 5, a space S is formed between two adjacent ribs 31e over the whole circumference at the circumferential direction of the inner-groove portion 31f. According to the present embodiment, the space S is formed to have a width and a depth suitable for the entrance of a pair of engaging fingers 63A disposed at a distal end portion of an engaging means 63 described below. According to the present embodiment, the space S may be formed at even intervals over the whole circumference at the circumferential direction of the pressing tube 31; however, it is not limited thereto.

As described below, according to the present embodiment, the inner-groove portion 31 and the plurality of ribs 31e are configured to form an engaging portion 32 for engaging a sheath 66 described below with the clip 10.

According to the present embodiment, during the period between the manufacture and the usage of the clip 10, the clip 10 is shipped as a clip cartridge 80 which is formed by accommodating the clip 10 in a housing 40. According to the clip cartridge 80 which is formed by accommodating the clip 10 in the housing 40, it is easy to ship the clip 10 and prevent the clip 10 from being exposed to the external environment and polluted. According to the present embodiment, FIG. 3 is shown for only explaining the positional relationship between the clip 10 and the housing 40 when the clip 10 is accommodated in the housing 40, and a shape or a configuration of the housing 40 is not limited thereto. The housing 40 may be formed by adapting any conventional configuration.

The members used to configure the clip 10 including the arm member 11 can be formed from the materials such as the cobalt chromium alloy, the titanium, the stainless steel and the like. The clip 10 is configured to be observable by the Nuclear Magnetic Resonance Imaging (MRI).

(Configuration of Applicator)

Figure 6:
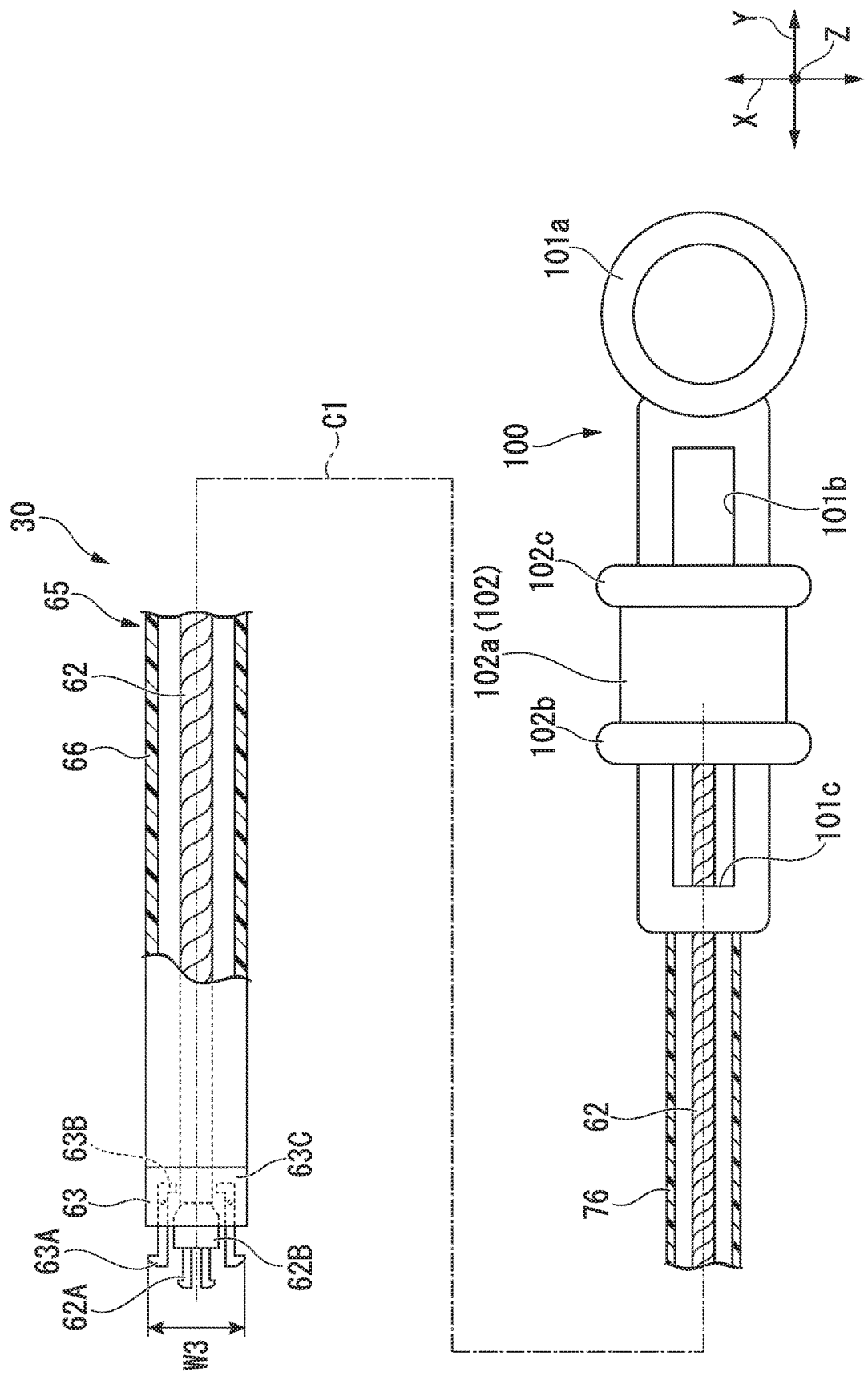
FIG. 6 is a partial cross-sectional view in a lateral view schematically showing a configuration of an applicator according to the present embodiment.

Next, the applicator 30 according to the present embodiment will be described with reference to FIG. 6. As shown in FIG. 6, the applicator 30 according to the present embodiment has an insertion portion 65 and an operation portion 100. The insertion portion 65 is positioned more distal than the operation portion 100 and connected to a distal end of the operation portion 100.

The insertion portion 65 of the applicator 30 has the sheath 66 and the operation wire 62. The sheath 66 is provided for accommodating the operation wire 62. The operation wire 62 is inserted into the sheath 66 so as to be advanceable/retractable in the sheath 66. The operation wire 62 is connected to a slider 102 of the operation portion 100 formed at the proximal end side of the applicator 30.

According to the present embodiment, the operation wire 62 is formed from a single metal wire or a twisted metal wire. As shown in FIG. 6, the operation wire 62 is configured to have the pair of hooks 62A provided at the distal end portion thereof to be elastically deformable and a fixation portion 62B formed more proximally than the pair of hooks 62A. The pair of hooks 62A are formed from the same metal material as that of the operation wire 62 so as to have the durability suitable for being repeatedly used. In the radial direction of the pressing tube 31, a width of the distal end portion of the operation wire 62 at which the pair hooks 62A are formed is larger than the width of the insertion portion 14A formed at the intermediate portion of the arm member 11 described above.

The fixation portion 62B is a tubular member formed from the metal material such as the stainless steel and the like. The width of the fixation portion 62B in the radial direction of the pressing tube 31 is equal to or larger than the width of the insertion port 14A in the intermediate portion 14 of the arm member 11. The operation wire 62 is fixed to the fixation portion 62B by various methods such as adhesion, welding, and the like. According to the present embodiment, the operation wire 62, the fixation portion 62B, and the pair of hooks 62A may be integrally formed. Accordingly, the pair of hooks 62A and the fixation portion 62B can be advanced/retracted together with the operation wire 62 due to the advance/retraction of the operation wire 62. The operation wire 62 can be connected to the arm member 11 by inserting the pair of hooks 62A into the arm member 11 via the insertion port 14A.

According to the present embodiment, the operation wire 62 is configured to transmit an operation force from an operator to operate the operation portion 100 along the longitudinal direction (for example, the operation of pushing the slider 102 and the operation of retracting the slider 102).

The sheath 66 may be formed as a coil sheath extending along the longitudinal axis C1 and formed from the stainless steel such as SUS301 and the like which has a high compression resistance strength. In this case, a coil formed by tightly winding an element wire (not shown) in the direction of axis Y can be used as the sheath 66. The sheath 66 is flexible while being strong with respect to the compressing force along the direction of the longitudinal axis C1.

As shown in FIG. 6, an engaging means 63 is provided at the distal end portion of the sheath 66. The engaging means 63 is configured for engaging the sheath 66 with the clip 10. For example, a configuration example of the engaging means 63 according to the present embodiment may be adapted by a cover 63C having a tubular shape and fixed to the distal end portion of the sheath 66, and a pair of engaging fingers (engaged portion) 63A formed on the inner circumferential surface of the cover 63C. Details will be described below, however, the sheath 66 and the clip 10 can be engaged and connected with each other by engaging the pair of engaging fingers 63A of the engaging means 63 with the inner-groove portion 31f of the pressing tube 31. According to the present embodiment, since the cover 63C is fixed to the distal end portion of the sheath 66, the engaging means 63 and the sheath 66 are integrally formed.

As shown in FIG. 6, in the direction orthogonal to the longitudinal direction of the sheath 66 (the direction of the axis X, the radial direction of the sheath 66), a distance between a pair of tails 63B formed at the proximal end side of the pair of engaging fingers 63A may be determined for the operation wire 62 to be suitably inserted through, and the distance may be smaller than the width of the fixation portion 62B provided at the distal end side of the operation wire 62. For example, the engaging means 63 has the configuration such that when the operator retracts the slider 102 of the operation portion 100, the fixation portion 62B provided at the distal end portion of the operation wire 62 moves proximally to come in contact the pair of tails 63B of the pair of engaging fingers 63A such that the pair of engaging fingers 63A rotate inwardly in the radial direction of the sheath 66 about an axis (not shown) as a rotation center (see FIG. 15).

However, the configuration of the engaging means 63 is not limited to the configuration shown in FIG. 6. According to the present embodiment, the engaging means 63 only has to be configured so as to make the engagement between the engaging means 63 and the inner-groove portion 31f is releasable when the operator moves the operation wire 62 toward the proximal end side relative to the sheath 66, in a state in which the engaging means (engaged portion) 63 is engaged with the inner-groove portion 31f of the pressing tube 31 (more specifically, the proximal wall 31f1 of the inner-groove portion 31f as the engaging portion), and the configuration of the engaging means 63 is not particularly limited. In other words, according to the present embodiment, the engagement between the engaging means 63 and the inner-groove portion 31f can be released by operating (retracting) the slider 102 of the operation portion 100 by the operator.

In the radial direction of the sheath 66, the width W3 of the pair of engaging fingers 63A in the engaging means 63 is larger than the width W1 of the small-diameter portion 31d of the pressing tube 31 described above. Accordingly, when the operator moves the operation wire 62 toward the distal end side to insert the engaging means 63 into the pressing tube 31 from the proximal end side of the pressing tube 31, the pair of engaging fingers 63A are pressed by the inner circumferential surface of the small-diameter portion 31d so as to be elastically deformed and inserted into the pressing tube 31. When the engaging means 63 reaches the position at which the inner-groove portion 31f is formed inside the pressing tube 31, the pressing due to the inner circumferential surface of the small-diameter portion 31d is released such that the pair of engaging fingers 63A enter the inner-groove portion 31 and the original width W3 is restored due to the elastic restoring force. Accordingly, the pair of engaging fingers 63A of the engaging means 63 are engaged with the inner-groove portion 31f of the pressing tube 31.

According to the present embodiment, the pair of engaging fingers 63A of the engaging means 63 may be biased outwardly in the radial direction of the sheath 66. Therefore, the pair of engaging fingers 63A can be definitely engaged inside the inner-groove portion 31f.

As shown in FIG. 5, at least part of distal end portions of the pair of engaging fingers 63A enter the space S such that a movement of the pair of engaging fingers 63A in the circumferential direction of the sheath 66 is limited by the ribs 31e. Accordingly, the width W3 of the pair of engaging fingers 63A is larger than the sum of the width W1 of the small-diameter portion 31d and the double difference between the depth h1 of the inner-groove portion 31f and the height H2 of the ribs 31e. In other words, according to the present embodiment, the width W3 of the pair of engaging fingers 63A satisfies Equation 1 shown below (see FIG. 9).

$$W3 > W1 + 2*(H1-H2) \quad \text{[Equation 1]}$$

As shown in FIG. 4 and FIG. 5, the pair of engaging fingers 63A can definitely enter the opening of the space S since the distance between any two adjacent ribs 31e in the circumferential direction of the pressing tube 31 (that is, an aperture amount AP of the space S) is appropriately determined according to the width of the pair of the engaging fingers 63A of the engaging means 63 in the circumferential direction. More specifically, by suitably setting the aperture amount AP of the space S, in the state in which at least part of the distal end portion of the pair of engaging fingers 63A enters the space S, in the circumferential direction of the pressing tube 31, there is almost no gap formed between each of the pair of engaging fingers 63A and the two adjacent ribs 31e.

As shown in FIG. 6, the operation portion 100 is configured to have an operation portion main body (handle) 101 and the slider 102.

The operation portion main body 101 is attached to the proximal end portion of the sheath 66. The operation portion main body 101 is formed in a rod shape extending in the direction of axis Y and the operation portion main body 101 has a finger ring 101a provided at the proximal end portion thereof. In the operation portion main body 101, a slit 101b is formed along the direction of axis Y.

The slider 102 is configured to be inserted through the operation portion main body 101. The slider 102 is slidable (advanceable and retractable) relative to the operation portion main body 101 in the direction of axis Y. According to the present embodiment, the operation wire 62 and the pair of hooks 62A provided at the distal end of the operation wire 62 advances and retracts due to the advancement and the retraction operations of the slider 102 in the direction of axis Y.

According to the present embodiment, the arm member 11 of the clip 10 advances or retracts together with the operation wire 62 due to the advancement and the retraction operations of the operation wire 62 in the state in which the operation wire 62 and the clip 10 are connected with each other. As a result, the first arm 12 and the second arm 13 of the arm member 11 can be opened or closed. However, according to the present embodiment, even the operation wire 62 is rotated in the circumferential direction, the rotation is not transmitted to the arm member 11 of the clip 10.

The slider 102 is formed in a cylindrical shape. On an outer circumferential surface of the slider 102, a recess portion 102a is formed over the whole circumference. The slider 102 is formed to have a flange portion 102b, the recess portion 102a, and a flange portion 102c in a sequence from the distal end side toward the proximal end side in the direction of axis Y. The pair of flange portions 102b, 102c are formed in elliptical shapes when viewed from the direction of axis Y respectively. Accordingly, the slider 102 is formed to be easy to grasp and it is possible to save space when the operation portion 100 is packed up. The slider 102 is engaged with the slit 101b formed in the operation portion main body 101 such that the movement range of the slider 102 relative to the operation portion main body 101 in the direction of axis Y is limited. According to the present embodiment, the operation portion 100 can be configured by adapting various configurations of the operation portion of the conventional endoscopic treatment instruments.

(Operation of Attaching Clip)

Next, operations of attaching the clip 10 to the applicator 30 according to the present embodiment will be described with reference to FIG. 7 to FIG. 10.

As shown in FIG. 7, in an initial state, the clip 10 according to the present embodiment is accommodated in the housing 40. In the housing 40, the clip 10 is in an open configuration such that the first arm 12 and the second arm 13 of the arm member 11 are separated from each other. The first arm 12 and the second arm 13 of the arm member 11 come in contact the tapered surface 31a at the distal end side of the pressing tube 31. On the other hand, the operator grasps the operation portion 100 and inserts the insertion portion 65 of the applicator 30 toward the clip 10 in the housing 40 in the longitudinal direction along the axis C1.

In this process, the pair of hooks 62A at the distal end portion of the operation wire 62 and the pair of engaging fingers 63A of the engaging means 63 are positioned at a position separated from the pressing tube 31 at the proximal end side of the pressing tube 31. The slider 102 of the operation portion 100 is not operated by the operator to advance or retract.

Next, as shown in FIG. 8, due to the operation of the operator, a part of the insertion portion 65 of the applicator 30, more specifically, the pair of hooks 62A at the operation wire 62 and the engaging means 63 enter the housing 40. As described above, the width W3 of the pair of engaging fingers 63A of the engaging means 63 is larger than the width W1 of the small-diameter portion 31d of the pressing tube 31 such that the pair of engaging fingers 63A enter the small-diameter portion 31d of the pressing tube 31 in the elastically deformed state and are disposed more proximally than the inner-groove portion 31f. The pair of hooks 62A of the operation wire 62 are positioned inside the small-diameter portion 31d.

In this state, the slider 102 of the operation portion 100 is not operated by the operator to advance or retract.

Figure 9B:
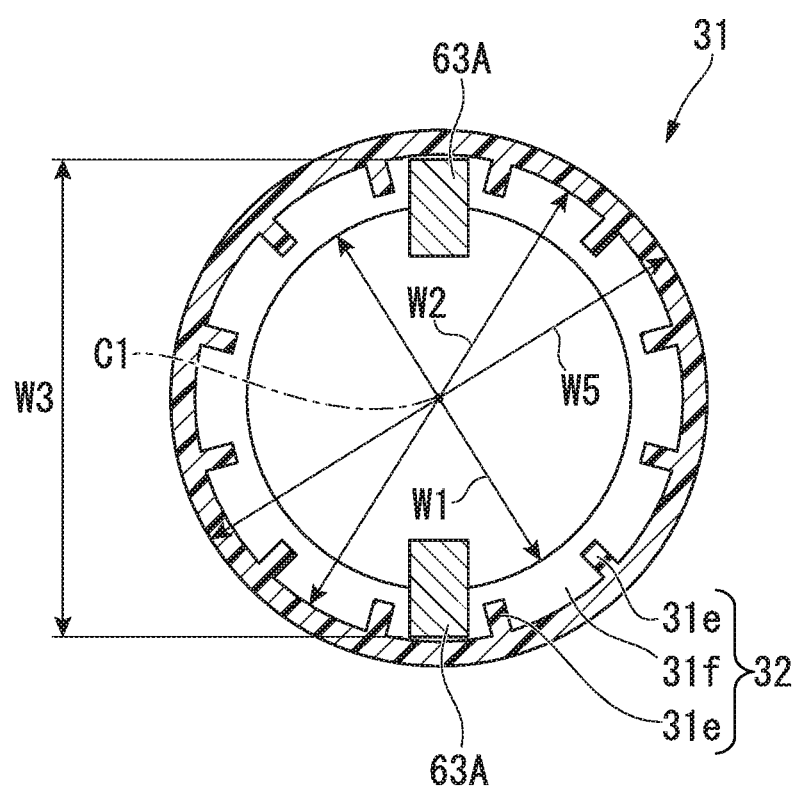
FIG. 9B is a view showing the operation for attaching the clip unit to the applicator according to the present embodiment.

Next, as shown in FIG. 9A and FIG. 9B, the operator inserts the insertion portion 65 of the applicator 30 into the housing 40 such that the pair of engaging fingers 63A of the engaging means 63 enter the inner-groove portion 31f formed in the small-diameter portion 31d of the pressing tube 31. At this time, due to the elastic restoring force of the pair of engaging fingers 63A, the width of the pair of engaging fingers 63A of the engaging means 63 restore to the width W3 in the radial direction. The width W3 of the pair of engaging fingers 63A satisfy the Equation 1 such that at least the part at the distal end side of the pair of engaging fingers 63A enter the space S formed in the inner-groove portion 31f, shown as FIG. 9A and FIG. 9B.

More specifically, as shown in FIG. 9A, in the longitudinal direction (the direction along the axis C1) of the clip 10 and the applicator 30, due to the own elastic restoring force, the pair of engaging fingers 63A of the engaging means 63 are moved in the radial direction (the direction intersecting the longitudinal direction) such that the pair of engaging fingers 63A come in contact the proximal wall (first surface) 31f1 of the inner-groove portion 31f. Accordingly, the movement of the pair of engaging fingers 63A of the engaging means 63 in the longitudinal direction is limited by the proximal wall 31f1 of the inner-groove portion 31f.

On the other hand, as shown in FIG. 9B, in the circumferential direction of the clip 10 and the applicator 30, each of the pair of engaging fingers 63A of the engaging means 63 enters the space S formed between two adjacent ribs 31e. As a result, each of the pair of engaging fingers 63A is sandwiched by the two adjacent ribs 31e in the circumferential direction. As described above, in the circumferential direction, since the engaging finger 63a and two adjacent ribs 31e are arranged to be close to each other and there is almost no gap formed between the engaging finger 63a and the rib 31e, the movement of the engaging finger 63A in the circumferential direction is limited by the rib 31e. In other words, in the circumferential direction of the pressing tube 31, the engaging finger 63A comes in contact a lateral surface (second surface) 31e1 of the adjacent rib 31e.

According to the present embodiment, in the inner-groove portion 31f, the lateral surface (second surface) of the rib 31e is arranged at a deeper side of the proximal wall (first surface) of the inner-groove portion 31f. Here, the phrase "deeper side" refers to a position in the inner-groove portion 31f which has a larger depth in the outwardly radial direction from the inner circumferential surface of the small-diameter portion 31d of the pressing tube 31. In other words, the phrase "arranged at a deeper side" means to be arranged at a position closer to the inner circumferential surface (second surface) 31f3.

Accordingly, as shown in FIG. 9A and FIG. 9B, the pair of engaging fingers 63A of the engaging means 63 come in contact the proximal wall 31f1 of the inner-groove portion 31f, and the pair of engaging fingers 63A are sandwiched by the adjacent ribs 31e such that the engaging means 63 is engaged with the inner-groove portion 31f. Accordingly, the pressing tube 31 of the clip 10 and the sheath 66 of the applicator 30 are connected with each other.

As shown in FIG. 9A, in the state when the pressing tube 31 and the sheath 66 are connected, the operator operates (push toward the distal end side) the slider 102 of the operation portion 100 to move the operation wire 62 toward the distal end side. By the operation, the pair of hooks 62A provided at the distal end side of the operation wire 62 pass through the insertion port 14A formed in the intermediate portion 14 of the arm member 11. During this process, the first arm 12 and the second arm 13 are contacting the distal end surface in the housing 40 such that the position of the arm member 11 inside the housing 40 is substantially maintained. The operator pushes the slider 102 of the operation portion 100 toward the distal end side to engage the pair of hooks 62A with the intermediate portion 14 of the arm member 11 such that the operation wire 62 and the arm member 11 of the clip 10 are connected with each other. At this time, a connecting portion of the operation wire 62 and the arm member 11 is positioned in the large-diameter portion 31c more distal than the step portion 31b in the pressing tube 31.

Figure 10A:
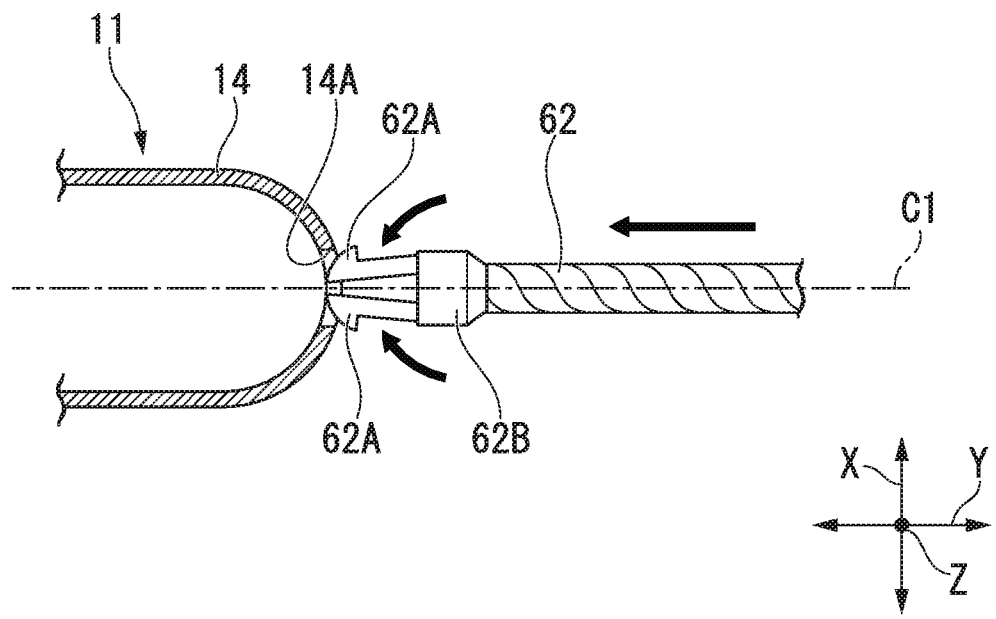
FIG. 10A is a view showing the operation for attaching the clip unit to the applicator according to the present embodiment.
Figure 10B:
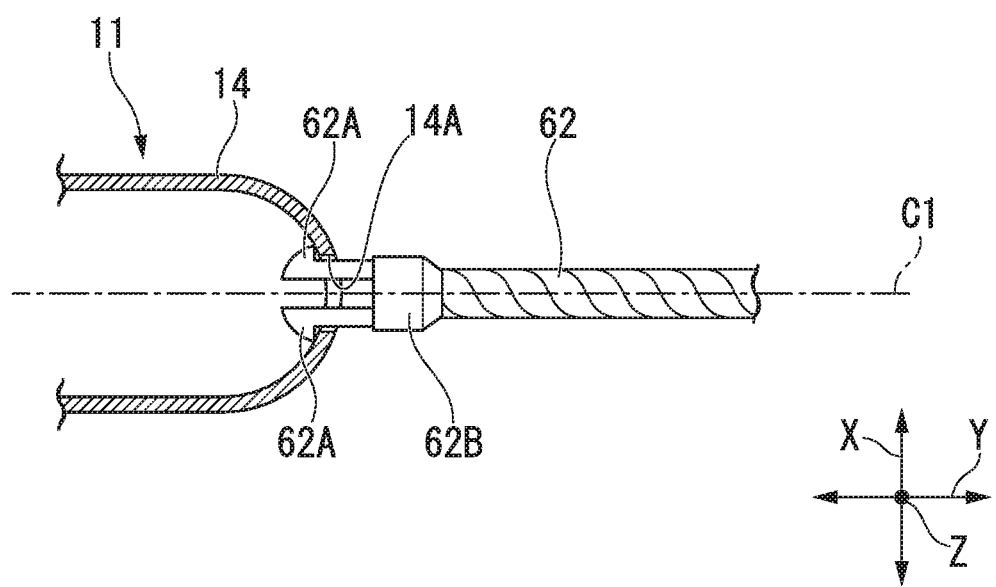
FIG. 10B is a view showing the operation for attaching the clip unit to the applicator according to the present embodiment.

More specifically, as shown in FIG. 10A and FIG. 10B, when the pair of hooks 62A provided at the distal end portion of the operation wire 62 contact the insertion port 14A formed in the intermediate portion 14 of the arm member 11, since the width of the pair of hooks 62A is larger than that of the insertion port 14A, inclined surfaces formed on the outer circumference of the pair of hooks 62A are contacting the edge of the insertion port 14A and the pair of hooks 62A are inserted into the insertion port 14A. As a result, the pair of hooks 62A are elastically deformed to pass through the insertion port 14A in a state in which the width of the pair of hooks 62A is reduced.

As shown in FIG. 10B, the engaged state is released when the pair of hooks 62A pass through the insertion port 14A. At this time, due to own elastic restoring force, the pair of hooks 62A are restored to the original width from the state in which the width is reduced and the pair of hooks 62A are engaged with the insertion port 14A. In this state, the state in which the pair of hooks 62A are engaged with the insertion port 14A is maintained even if the operator advances or retracts the slider 102 in the longitudinal direction. When the operator rotates the slider 102 about the longitudinal axis (axis C1), the pair of hooks 62A rotate about the longitudinal axis together with the operation wire 62A; however, the rotation force of the rotation wire 62 is not transmitted to the arm member 11. Accordingly, when the operator rotates the slider 102 about the longitudinal axis, the pair of hooks 62A are rotated relative to the arm member 11.

As shown in FIG. 10B, the fixation portion 62B provided at the proximal end side of the pair of hooks 62A has a width larger than that of the insertion port 14A. Accordingly, the operator pushes the slider 102 to make the fixation portion 62B to contact the edge of the insertion port 14A so as to push the arm member 11 toward the distal end side.

When the operator has confirmed that the operation wire 62 and the arm member 11 are engaged with each other, the operator can hold the operation portion 100 and retract the clip 10 and the operation wire 62 together to remove them from the housing 40. In this state, as shown in FIG. 11, the clip 10 and the applicator 30 are connected with each other in a state in which the pair of engaging fingers 63A of the engaging means 63 of the applicator 30 is engaged with the inner-groove portion 31f of the pressing tube 31 of the clip 10, and the pair of hooks 62A of the operation wire 62 are engaged with the arm member 11 of the clip 10.

According to the operations described above, the operations for attaching the clip 10 to the applicator 30 are finished and the medical instrument (ligation device) 1 according to the present embodiment is configured (see FIG. 11).

According to the present embodiment, since the pair of hooks 62A of the operation wire 62 are engaged with the arm member 11, when the operator advances and retracts the slider 102, it is possible to make the arm member 11 of the clip 10 connected with the operation wire 62 to advance and retract relative to the pressing tube 31. When the arm member 11 advances and retracts relative to the pressing tube 31, the first arm 12 and the second arm 13 of the arm member 11 can be opened and closed respectively. In other words, when the operator advances and retracts the slider 102, it is possible to make the arm member to transfer between the open configuration and the close configuration.

In this process, due to the operations of the operator with respect to the slider 102, it is possible that the pressing tube 31 moves toward the distal end side while the arm member 11 is advanced or retracted. However, the pair of engaging fingers 63A of the engaging means 63 are engaged with the proximal wall (first surface) 31f1 in the inner-groove portion 31f such that the movement of the pressing tube 31 toward the distal end side is restricted. In other words, the pair of engaging fingers 63A are engaged with the proximal wall (first surface) 31f1 in the inner-groove portion 31f such that the separation of the pressing tube 31 and the sheath 66 are restricted and avoided.

According to the present embodiment, when the pair of engaging fingers 63A of the engaging means 63 are engaged with the inner-groove portion 31f of the pressing tube 31, the engaging finger 63A is engaged in the space S formed between the two adjacent ribs 31e. Accordingly, the movement (rotation) of the pair of the engaging fingers 63A of the engaging means 63 in the circumferential direction is restricted by the two corresponding ribs 31e. In other words, in the circumferential direction, each of the pair of the engaging fingers 63A and the corresponding ribs 31e can rotate integrally. Accordingly, when the operator operates the operation portion 100 to rotate the sheath 66, the pair of engaging fingers 63A of the engaging means 63 fixed to the distal end side of the sheath 66 transmits the rotation operation force to the ribs 31e to rotate the pressing tube 31. Furthermore, according to the present embodiment, the first arm 12 and the second arm 13 of the arm member 11 contact the tapered surface 31a at the distal end side of the pressing tube 31 due to their own elastic restoring forces. Accordingly, when the rotation operation force by the operator makes the pressing tube 31 to rotate, the arm member 11 can rotate together with the pressing tube 31.

As described above, according to the present embodiment, due to the engagement of the engaging portion 32 (inner-groove portion 31f and ribs 31e) provided in the pressing tube 31 of the clip 10 and the engaging means 63 provided in the applicator 30, the advancement/retraction operation and the rotation operation of the arm member 11 of the clip 10 can be restricted respectively. More specifically, in the state in which the clip 10 is attached to the applicator 30, the rotation operation force by the operator to operate the operation portion 100 for rotating the sheath 66 can be definitely transmitted to the pressing tube 31 and the arm member 11 of the clip 10. In other words, according to the present embodiment, it is possible to avoid the pressing tube 31 of the clip 10 from idling rotating without following the rotation of the sheath 66.

According to the present embodiment, the inner-groove portion 31f is formed over the whole circumference of the inner circumferential surface of the pressing tube 31 of the clip 10, and the plurality of ribs 31e are formed at even intervals in the inner-groove portion 31f. Accordingly, when the operator operates the operation portion 100 to move (advance) the sheath 66 toward the clip 10 accommodated in the housing 40, it is not necessary to match the phrases of the sheath 66 and the pressing tube 31 in the circumferential direction. In other words, in spite of the relative positional relationship between the sheath 66 and the pressing tube 31 in the circumferential direction about the longitudinal axis (axis C1) of the clip 10 and the applicator 30, the pair of engaging fingers 63A of the engaging means 63 can be engaged inside the inner-groove portion 31f.

More specifically, according to the present embodiment, as shown in FIG. 5, in the radial direction of the pressing tube 31, the height H2 of the ribs 31e is smaller than the depth H1 of the inner-groove portion 31f. Accordingly, for example, when the applicator 30 is advanced along the longitudinal direction to the position at which the inner-groove portion 31f is formed, the engaging finger 63A moves outwardly in the radial direction intersecting with the longitudinal direction of the pressing tube 31 and enters the inner-groove portion 31f due to the elastic restoring force. At this time, it is possible that the engaging finger 63A contacts with the ribs 31e when the engaging finger 63A moves outwardly in the radial direction inside the inner-groove portion 31f. However, in this case, due to the elastic restoring force, the movement of the engaging finger 63A outwardly in the radial direction is not obstructed by the ribs 31e and the engaging finger 63A can be accommodated in the space S. In other words, according to the present embodiment, when the applicator 30 is advanced toward the clip 10 accommodated in the housing 40 along the longitudinal direction of the pressing tube 31, it is impossible that the pair of engaging fingers 63A of the engaging means 63 move beyond the inner-groove portion 31f so as to be more distal than the inner-groove portion 31f.

(Procedures by Medical Instrument)

Next, procedures for treating the target tissue T using the medical instrument (ligation device) 1 will be described with reference to FIG. 11 to FIG. 16, wherein the medical instrument 1 is configured by attaching the clip 10 to the applicator 30 by the operations described above.

As shown in FIG. 11, when the clip 10 is taken out from the housing 40 of the clip cartridge 80 in the state of being attached to the applicator 30, the arm member 11 is in the open configuration in which the first arm 12 and the second arm 13 of the arm member 11 contact the tapered surface 31a formed at the distal end side of the pressing tube 31 while being separated from each other due to their own elastic restoring forces respectively. The pair of engaging fingers 63A of the engaging means 63 of the applicator 30 are engaged with the inner-groove portion 31f of the pressing tube 31. The pair of hooks 62A of the operation wire 62 are engaged with the intermediate portion 14 of the arm member 11. The connection portion between the operation wire 62 and the arm member 11 is positioned more distally than the step portion 31b in the pressing tube 31. The pair of protrusions 16, 17 formed on the arm member 11 is positioned more distally than the step portion 31b in the pressing tube 31.

The operator inserts the endoscope (not shown) into the body of the patient. The operator inserts the medical instrument 1 from the proximal end portion of the channel of the endoscope, protrudes the medical instrument 1 from the distal end portion of the channel of the endoscope, and moves the medical instrument 1 to the position near the target tissue T as the treatment target. During this process, the close configuration of the arm member 11 is kept such that the first arm 12 and the second arm 13 of the arm member 11 are closed due to the operations of the operator such as continuously holding the slider 102 and the like.

When the operator inserts the medical instrument 1 via the through the channel of the endoscope and guides the medical instrument 1 to the vicinity of the target tissue T, as shown in FIG. 11, the operator transfers the arm member 11 from the close configuration to the open configuration. In this state, the pair of engaging fingers 63A of the engaging means 63 are engaged with the inner-groove portion 31f of the pressing tube 31, and the pair of hooks 62A of the operation wire 62 are engaged with the intermediate portion 14 of the arm member 11.

In the state shown in FIG. 11, the operator confirms both of the opening-width of the arm member 11 and the size of the target tissue T. For example, in a case when the opening-width of the arm member 11 is smaller than the size of the target tissue T, the operator can operate the operation portion 100 to adjust the opening-width of the arm member 11.

More specifically, according to the present embodiment, the operator can advance and retract the arm member 11 together with the operation wire 62 by advancing and retracting the slider 102 of the operation portion 102 respectively. As described above, when the operator advances and retracts the arm member 11, the pair of engaging fingers 63A are engaged with the proximal wall 31f1 of the inner-groove portion 31f of the pressing tube 31 such that the pressing tube 31 does not advance and retract together with the arm member 11 respectively. Accordingly, when the operator advances and retracts the slider 102, the arm member 11 advances and retracts relative to the pressing tube 31 so as to adjust the opening-width between the first arm 12 and the second arm 13 of the arm member 11.

On the other hand, the operator confirms the orientation of the arm member 11 according to the orientation and the shape of the target tissue T. The operator can adjust the orientation of the arm member 11 for suitably grasping the target tissue T.

In this case, for example, the operator holds the operation portion 100 and rotates the operation portion 100 for rotating the sheath 66 about the longitudinal axis (axis C1). As described above, in the inner-groove portion 31f of the pressing tube 31, each of the pair of engaging fingers 63A is sandwiched by two corresponding ribs 31e such that the movement in the circumferential direction is restricted (see FIG. 9B). In this state, when the operator rotates the sheath 66, due to the engagement of the pair of engaging fingers 63A and the ribs 31e, the rotation operation force by the operator is transmitted to the pressing tube 31 and then applied to the first arm 12 and the second arm 13 of the arm member 11 which contact the tapered surface 31a at the distal end side of the pressing tube 31. As a result, the arm member 11 of the clip 10 rotates about the longitudinal axis following the rotation of the sheath 66 so as to adjust the orientation of the clip 10 according to the shape of the target tissue T.

According to the present embodiment, even if the operator rotates the operation wire 62, the pair of hooks 62A provided at the distal end side of the operation wire 62 cannot transmit this rotation operation force to the arm member 11. Accordingly, even in the case when the operator inserts the medical instrument 1 according to the present embodiment into the complicated internal environment in the body, it is possible to prevent the operation wire 62 from meandering such that the rotation operation force cannot be suitably transmitted to the arm member 11. In other words, even in the case when the medical instrument 1 according to the present embodiment is inserted into the complicated internal environment in the body, the effect of suitably transmitting the rotation operation force to the arm member 11 by the sheath 66 can be achieved.

As shown in FIG. 11, by the operations described above, it is possible to put the target tissue T between the first arm 12 and the second arm 13 of the arm member 11 in the open configuration. When the operator confirms that the target tissue T is positioned between the first arm 12 and the second arm 13, the operator can operate the endoscope to hold the target tissue T by the first arm 12 and the second arm 13 of the arm member 11.

When the operator confirms that the target tissue T is positioned between the first arm 12 and the second arm 13, the operator holds the operation portion main body 101 to retract the slider 102. At this time, the operation wire 62 moves toward the proximal end side together with the first arm 12 and the second arm 13. In the state in which the intersecting portion of the first arm 12 and the second arm 13 enters the pressing tube 31, the first arm 12 and the second arm 13 contact the tapered surface 31a formed on the distal end side of the pressing tube 31 such that the first arm 12 is elastically deformed toward the second arm 13 side and the second arm 13 is elastically deformed toward the first arm 12 side. As a result, the distal end portions of the first arm 12 and the second arm 13 approaches each other to cause the opening-width of the arm member 11 to be reduced, that is, the arm member 11 is transferred from the open configuration to the close configuration.

Figure 12:
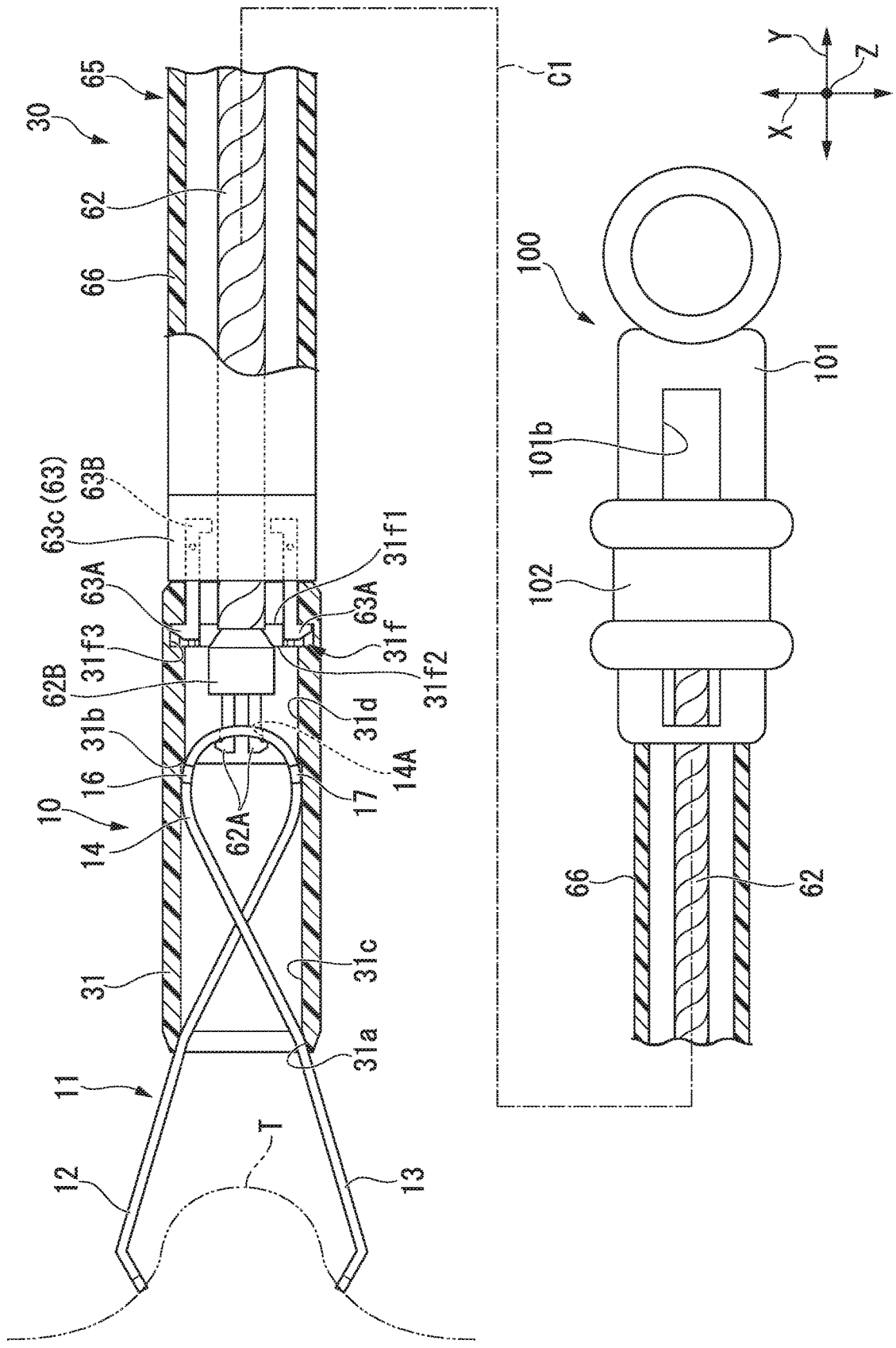
FIG. 12 is a view showing an operation for treating a target issues using the medical instrument according to the present embodiment.

As shown in FIG. 11 and FIG. 12, during the process when the operator retracts the slider 102 toward the proximal end side, the proximal end portion of the arm member 11 including the intermediate portion 14 is retracted toward the proximal end side in the pressing tube 31. According to the present embodiment, the operator can push the slider 102 toward the distal end side until the pair of protrusions 16, 17 provided at the proximal end portion of the arm member 11 contact the step portion 31b of the pressing tube 31 to move the arm member toward the distal end side. In other words, the operator can push the slider 102 toward the distal end side until the pair of protrusions 16, 17 provided at the proximal end portion of the arm member 11 contact the step portion 31b of the pressing tube 31 to transfer the arm member to the open configuration. Due to the operations, the operator can use the arm member 11 to grasp the target tissue T again.

That is, in the process of retracting the slider 102 unit the state described above, the operator can operate the endoscope to direct the clip 10 toward the target tissue T again. Subsequently, the operator can grasp the target tissue T using the clip 10 again according to the procedures described above.

When the operator confirms that the target tissue T is grasped and held by the arm member 11 in the close configuration in a desired state, the operator can retract the slider 102 toward the proximal end side until the pair of protrusions 16, 17 provided at the arm member 11 move beyond the step portion 31b to be positioned in the small-diameter portion 31d in the pressing tube 31. In this state, since the pair of protrusions 16, 17 bite into the inner wall of the small-diameter portion 31d of the pressing tube 31, the movement of the arm member 11 toward the distal end side is restricted. In other words, when the pair of protrusions 16, 17 are positioned in the small-diameter portion 31d in the pressing tube 31, the state in which the target tissue T is held by the arm member in the close configuration is locked. Accordingly, in this state, the operator cannot perform the operations to grasp the target tissue T again. As shown in FIG. 13, the root of the target tissue T is tightly held by the first arm 12 and the second arm 13, and the configuration of the arm member 11 in which the distance between the first arm 12 and the second arm 13 is substantially zero is included in the close configuration of the arm member 11.

In this state, both of the engagement between the pair of engaging fingers 63A of the engaging means 63 and the inner-groove portion 31f of the pressing tube 31, and the engagement between the pair of hooks 62A of the operation wire 62 and the arm member 11 are maintained.

Figure 14:
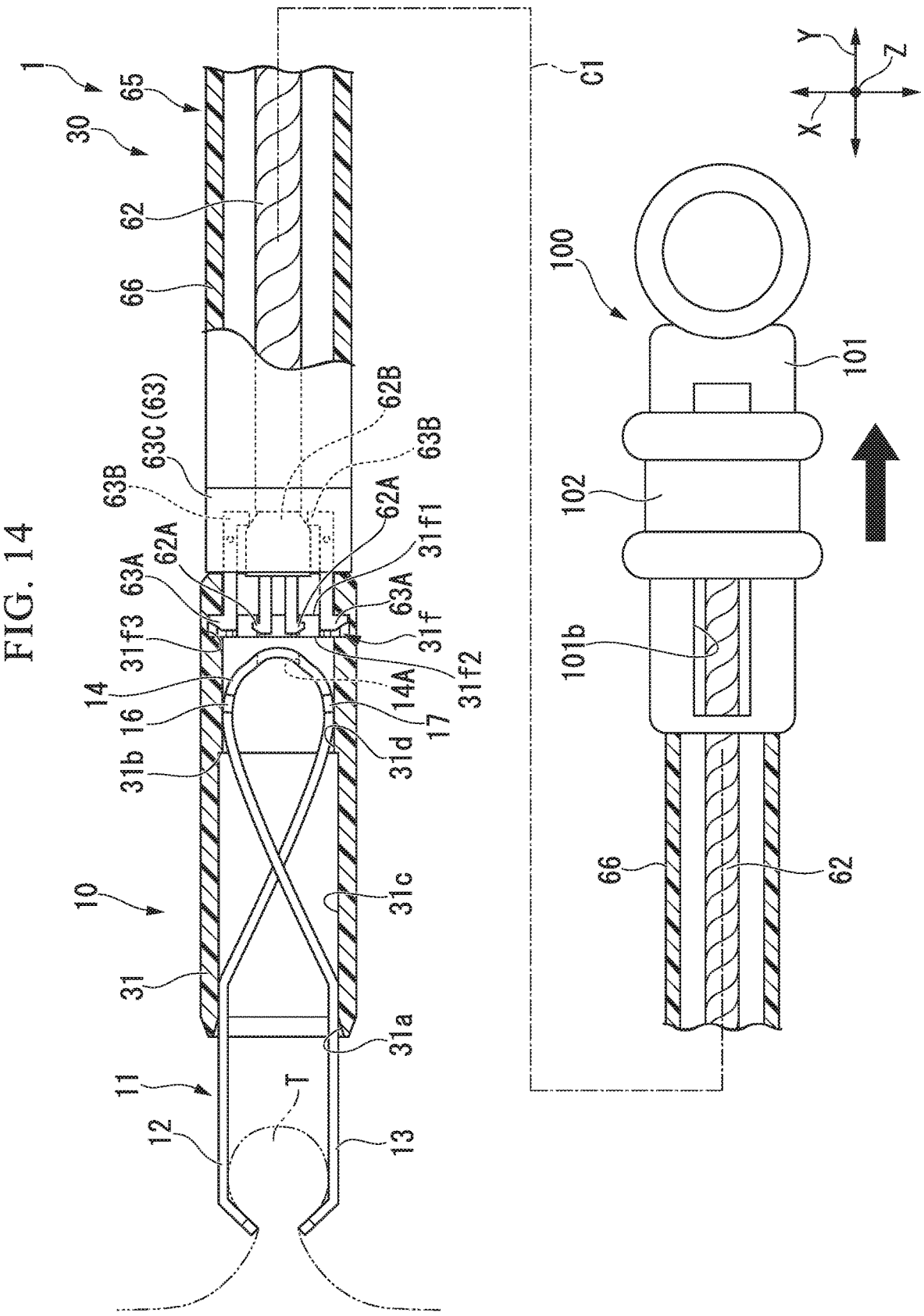
FIG. 14 is a view showing an operation for treating a target issues using the medical instrument according to the present embodiment.

Afterwards, the operator separates the clip 10 ligating the target tissue T from the applicator 30 and leave the clip 10 only in the body. Specifically, when the operator further retracts the slider 102 toward the proximal end side, the retraction force is applied to the connection portion of the operation wire 62 and the clip 10. According to the present embodiment, the strength of the intermediate portion 14 of the arm member 11 is set to be lower than that of other parts. Accordingly, as shown in FIG. 14, when the retraction force applied to the connection portion of the operation wire 62 and the clip 10 exceeds a predetermined value, the intermediate portion 14 of the arm member 11 is deformed and the width of the insertion port 14A formed at the intermediate portion 14 is enlarged.

As a result, the pair of hooks 62A of the operation wire 62 are extracted and removed from the insertion port 14A. According to the present embodiment, the pair of hooks 62A, for example, are formed from the metal materials and have a high strength such that neither deformation nor damage can be found in the pair of hooks 62A. At this time, the state in which the target tissue T is held by the clip 10 which is configured from the arm member 11 and the pressing tube 31 is maintained. At this case, the intermediate portion 14 in the arm member 11 is deformed; however, the case in which fragments generated due to the broken arm member 11 and the operation wire 62 are unintentionally left in the body does not occur.

Figure 15:
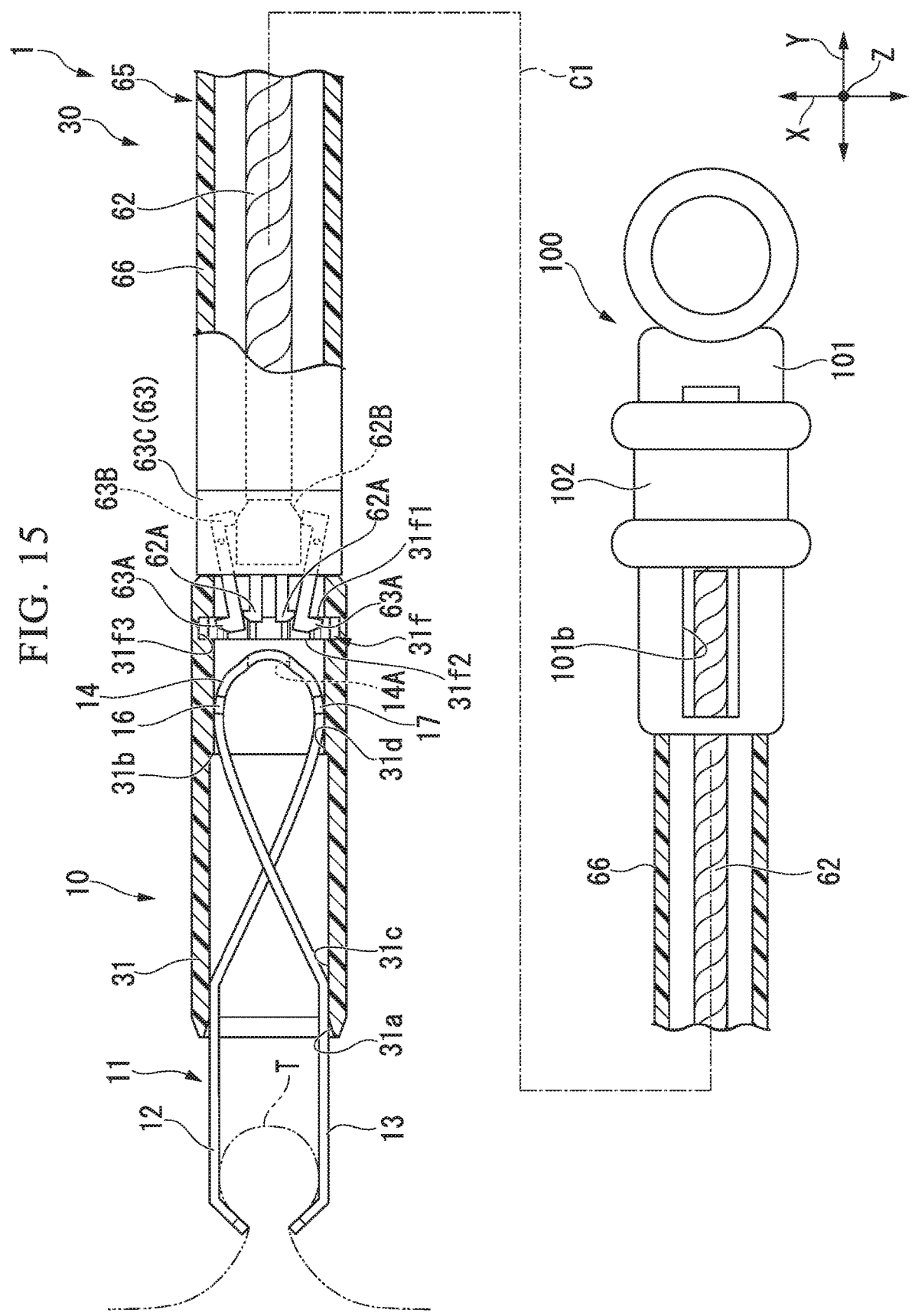
FIG. 15 is a view showing an operation for treating a target issues using the medical instrument according to the present embodiment.

Afterwards, the operator operates the operation portion 100 to release the engagement between the sheath 66 and the pressing tube 31 for separating the clip 10 from the applicator 30. Specifically, as shown in FIG. 15, when the operator retracts the slider 102 of the operation portion 100 toward the proximal end side, the pair of tails 63B of the engaging means 63 come in contact the fixation portion 62B provided at the distal end side of the operation wire 62. In this state, when the operator further retracts the slider 102 of the operation portion 100 toward the proximal end side, the fixation portion 62B of the operation wire 62 presses the pair of tails 63B so as to make the pair of engaging fingers 63A to rotate inwardly in the radial direction about an axis (not shown) as the rotation center. Due to these operations, the engagement between the pair of engaging fingers 63A and the inner-groove portion 31f of the pressing tube 31 is released.

Figure 16:
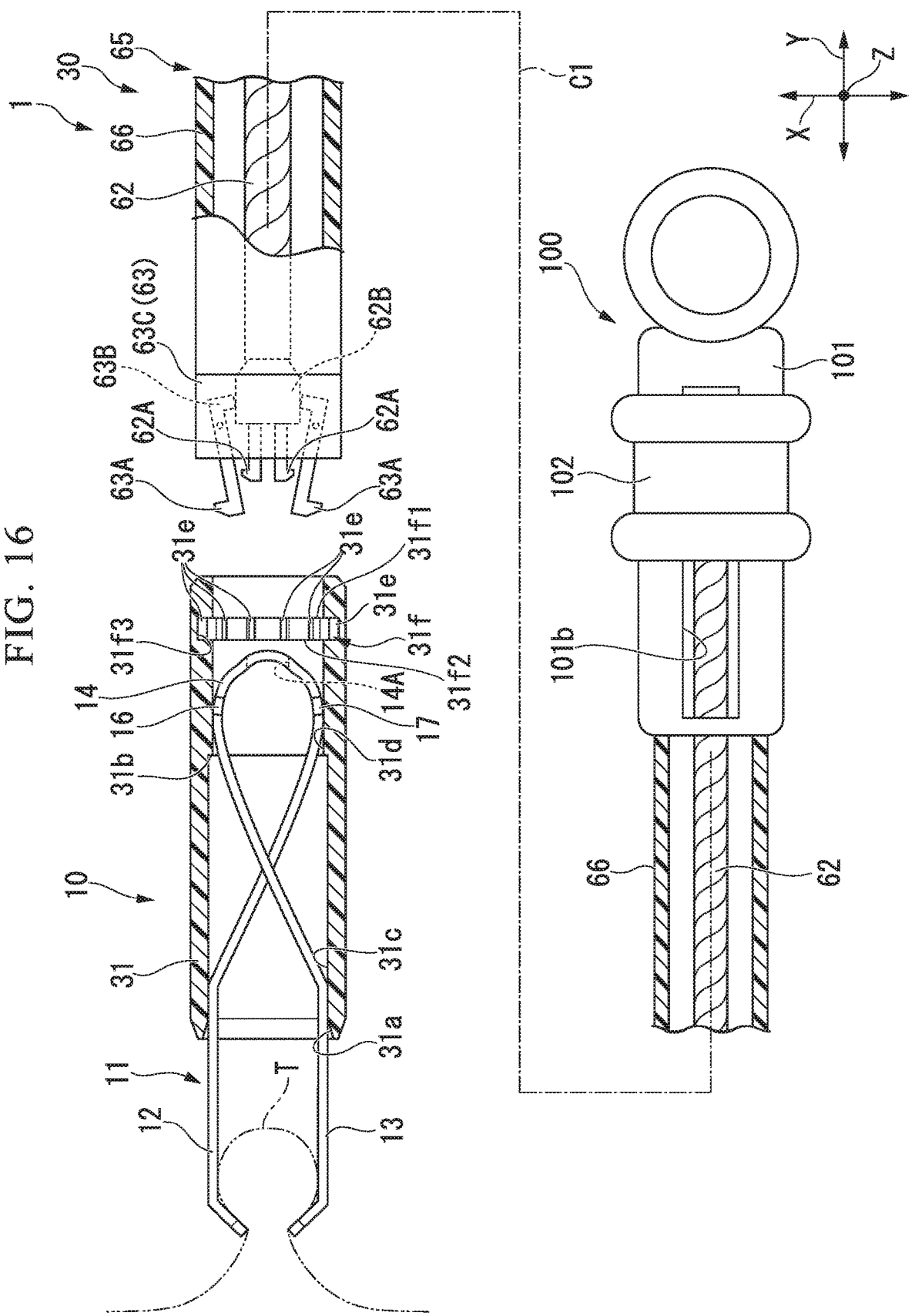
FIG. 16 is a view showing an operation for treating a target issues using the medical instrument according to the present embodiment.

Subsequently, the operator retracts the slider 102 of the operation portion 100 toward the proximal end side to separate the engaging means 63 including the pair of engaging fingers 63A from the pressing tube 31. As shown in FIG. 16, the clip 10 holding the target tissue T is separated from the applicator 30 and indwelled inside the body. On the other hand, the operator takes the applicator out from the channel of the endoscope and performs necessary operations to finish the procedures.

(Effects)

According to the medical instrument 1 of the present embodiment, since the pair of engaging fingers 63A of the engaging means 63 are engaged with the proximal wall 31f1 of the inner-groove portion 31f, the movement of the pressing tube 31 relative to the sheath 66, that is, the separation of the pressing tube 31 and the sheath 66 is restricted. Since the pair of engaging fingers 63A of the engaging means 63 are engaged with the plurality of ribs 31e in the inner-groove portion 31f, the pressing tube 31 can rotate following the rotation of the sheath 66. In other words, the arm member 11 of the clip can rotate following the rotation of the sheath 66.

Therefore, according to the medical instrument 1 according to the present embodiment, when the operator operates the sheath 66 to rotate the arm member 11 for adjusting the orientation thereof, it is possible to prevent the idling rotation of the pressing tube 31 and prevent that the rotation operation force from the sheath 66 to the arm member 11 cannot be transmitted.

In the medical instrument 1 according to the present embodiment, the operator can advance and retract the slider 102 of the operation portion 100 until the pair of protrusions 16, 17 provided at the arm member 11 move beyond the step portion 31b to a more proximal position in the pressing tube 31 to adjust the close configuration and the open configuration of the arm member 11 for repeatedly grasping the target tissue T.

In the medical instrument 1 according to the present embodiment, on the inner circumferential surface of the pressing tube 31, the inner-groove portion 31f is formed over the whole circumference, and the plurality of the ribs 31e are provided in the inner-groove portion 31f by even intervals. Accordingly, during the operations of attaching the clip 10 to the applicator 30 by the operator, in the circumferential direction about the longitudinal axis (axis C1), in spite of the relative positional relationship of the sheath 66 and the pressing tube 31, it is possible to engage the engaging means 63 fixed at the distal end portion of the sheath 66 with the inner-groove portion 31f formed in the pressing tube 31 only by moving the applicator 30 toward the clip 10 that is accommodated in the housing 40 along the longitudinal direction. In other words, according to the medical instrument 1 according to the present embodiment, during the operations of attaching the clip 10 to the applicator 30, since it is not necessary to match the orientations of the applicator 30 and the clip 10 in the circumferential direction, it is easy for the operator to perform the operations.

First Modification

Next, the first modification of the present embodiment will be described with reference to FIG. 17A and FIG. 17B. In various modifications of the present embodiment including the present first modification and various embodiments that will be described below, same configurations with that of the medical instrument 1 according to the first embodiment described above will be assigned with the same numerals and the description will be omitted, and only the difference from the first embodiment will be mainly described.

The clip 10A according to the present modification is different from the clip 10 according to the first embodiment in the configuration of the pressing tube 31A. FIG. 17A is a view showing a state in which the clip 10A according to the present modification is accommodated in the housing 40. FIG. 17B is the cross-sectional view of the pressing tube 31A which is broken along XVIIB-XVIIB line in the FIG. 17A.

Figure 17A:
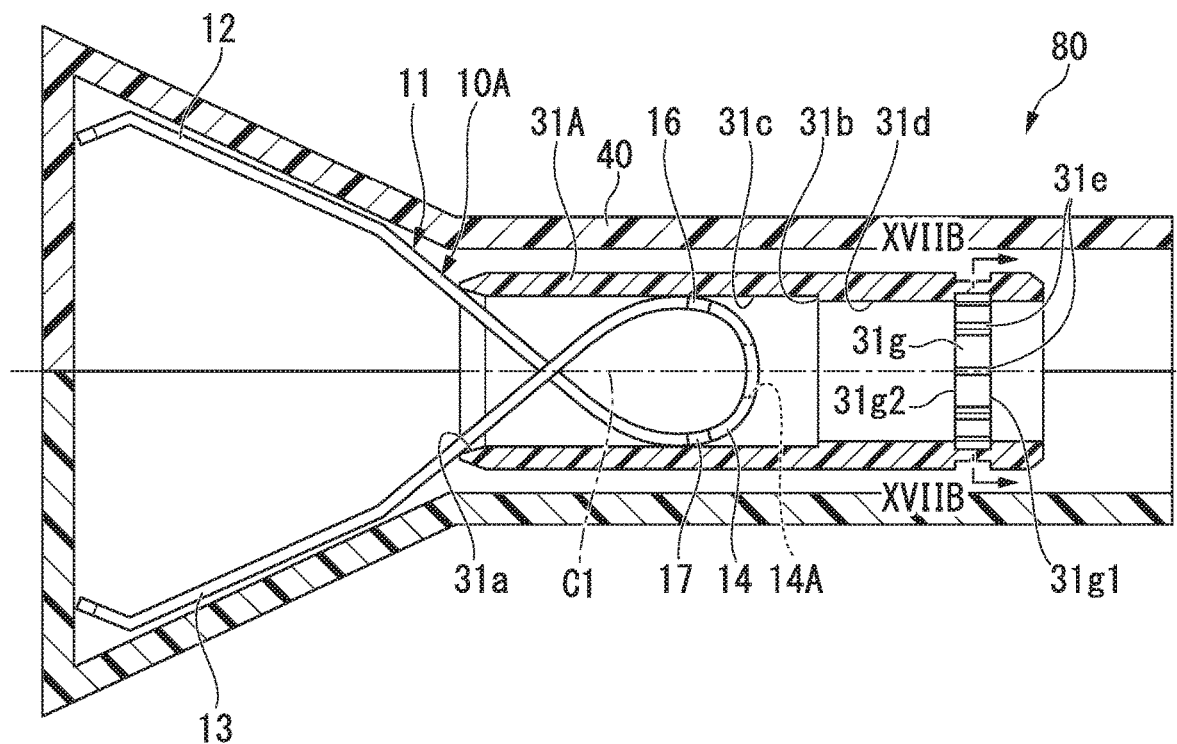
FIG. 17A is a partial cross-sectional view in a lateral view schematically showing a configuration of a clip unit according to a first modification of the present embodiment.
Figure 17B:
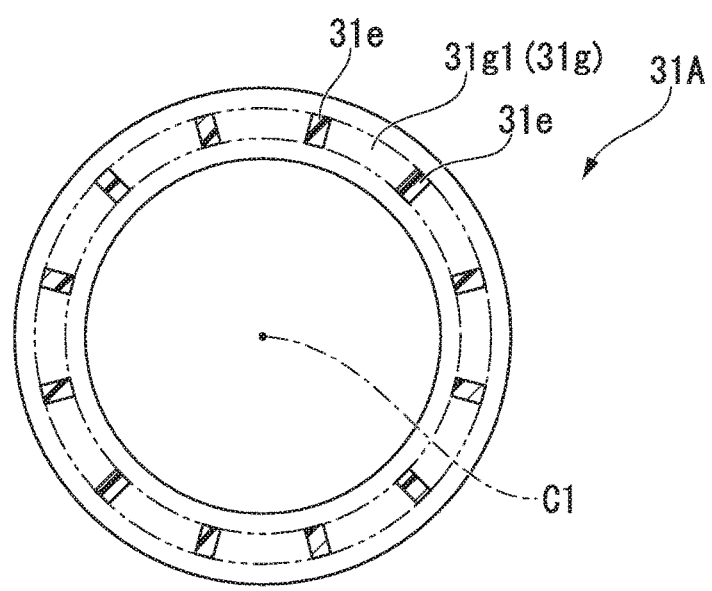
FIG. 17B is a cross-sectional view along the line XVIIB-XVIIB in the FIG. 17A.

As shown in FIG. 17A, the clip 10A according to the present modification has a window portion 31g formed in the small-diameter portion 31d more proximal than the step portion 31b of the pressing tube 31 over the whole circumference of the pressing tube 31, wherein the window portion 31g is formed to penetrate the pressing tube 31A in the radial direction. In the same manner as in the first embodiment, the plurality of ribs 31e is formed in the window portion 31g at even intervals in the circumferential direction of the pressing tube 31A. In other words, in the window portion 31g, the proximal wall (first surface) 31g1 and the distal wall 31g2 are connected by the plurality of ribs 31e. Other configurations of the clip 10A according to the present modification are the same as the configurations of the clip 10 according to the first embodiment.

The pressing tube 31A of the clip 10A, for example, can be manufactured by connecting two tubular members with the plurality ribs 31e using adhesion or welding method. Accordingly, the pressing tube 31A can be manufactured with a simple method to reduce the manufacture cost of the clip 10A.

In the clip 10A according to the present modification, in the same manner as in the first embodiment, the operator can engage the pair of engaging fingers 63A of the engaging means 63 with the proximal wall 31g1 of the window portion 31g by moving the applicator 30 toward the clip 10A along the longitudinal direction (direction of axis C1). According to the present modification, since the pair of engaging fingers 63A of the engaging means 63 are engaged with the proximal wall 31g1 of the window portion 31g, the movement of the pressing tube 31A toward the distal end side relative to the sheath 66, and the separation of the pressing tube 31A and the sheath 66 can be restricted.

It is possible to configure the medical instrument 1 having same effects as that of the first embodiment by attaching the clip 10A according to the present modification to the applicator 30.

Second Modification

Figure 18A:
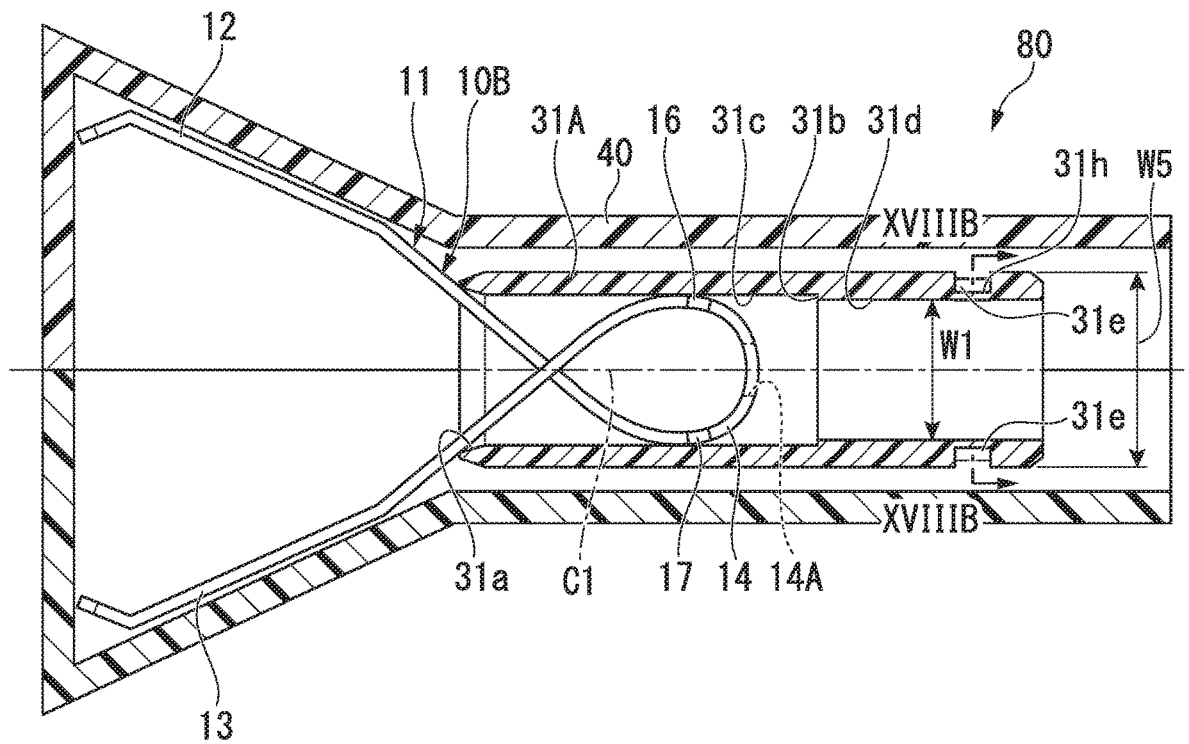
FIG. 18A is a partial cross-sectional view in a lateral view schematically showing a configuration of a clip unit according to a second modification of the present embodiment.
Figure 18B:
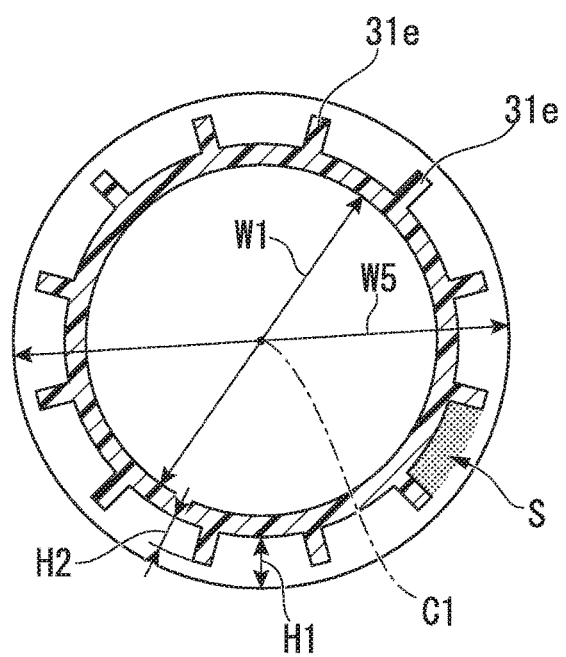
FIG. 18B is a cross-sectional view along the line XVIIIB-XVIIIB in the FIG. 18A.

Next, a second modification of the present embodiment will be described with reference to FIG. 18A to FIG. 20B. FIG. 18A is a view showing the state in which the clip 10B according to the present modification is accommodated in the housing 40. FIG. 18B is a cross-sectional view of the pressing tube 31B broken along XVIIIB-XVIIIB line in FIG. 18A.

As shown in FIG. 18A and FIG. 18B, the clip 10B according to the present modification has an outer-groove portion 31h formed in the small-diameter portion more proximal than the step portion 31b of the pressing tube 31B, wherein the outer-groove portion 31h is formed over the whole circumference about the longitudinal axis (axis C1), and the outer-groove portion 31h is formed by cutting and removing part of the pressing tube 31B from the outer circumferential surface inwardly in the radial direction of the pressing tube 31b. In other words, the thickness of the part at which the outer-groove portion 31h is formed, is thinner than other parts of the pressing tube 31b of the clip 10B. In the outer-groove portion 31h, the plurality of ribs 31e are formed at even intervals over the whole circumference. As shown in FIG. 18B, the plurality of ribs 31e are formed to protrude outwardly in the radial direction of the pressing tube 31B from the inner circumferential surface 31h3 of the outer-groove portion 31h. In the present modification, the depth H1 of the outer-groove portion 31h is set to be larger than the height H2 of the plurality of ribs 31e. Accordingly, in the outer-groove portion 31h, the plurality of ribs 31 do not protrude outwardly in the radial direction from the outer circumferential surface of the pressing tube 31B.

Figure 19:
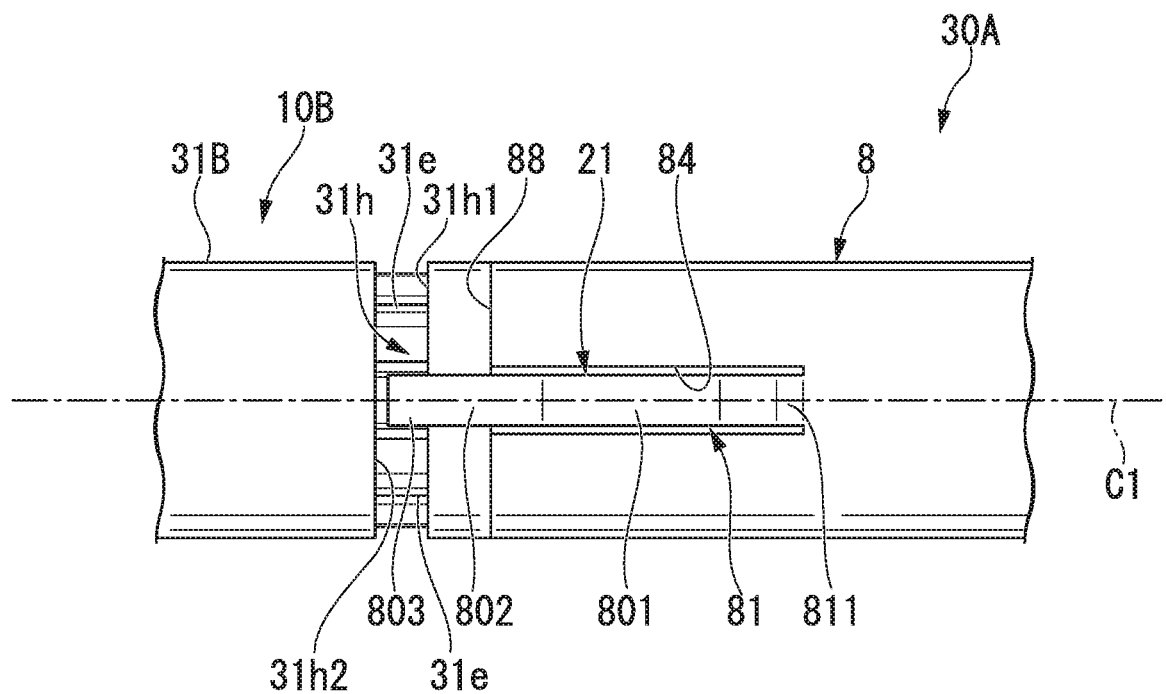
FIG. 19 is a lateral view showing a configuration of part of an applicator according to the second modification of the present embodiment.
Figure 20A:
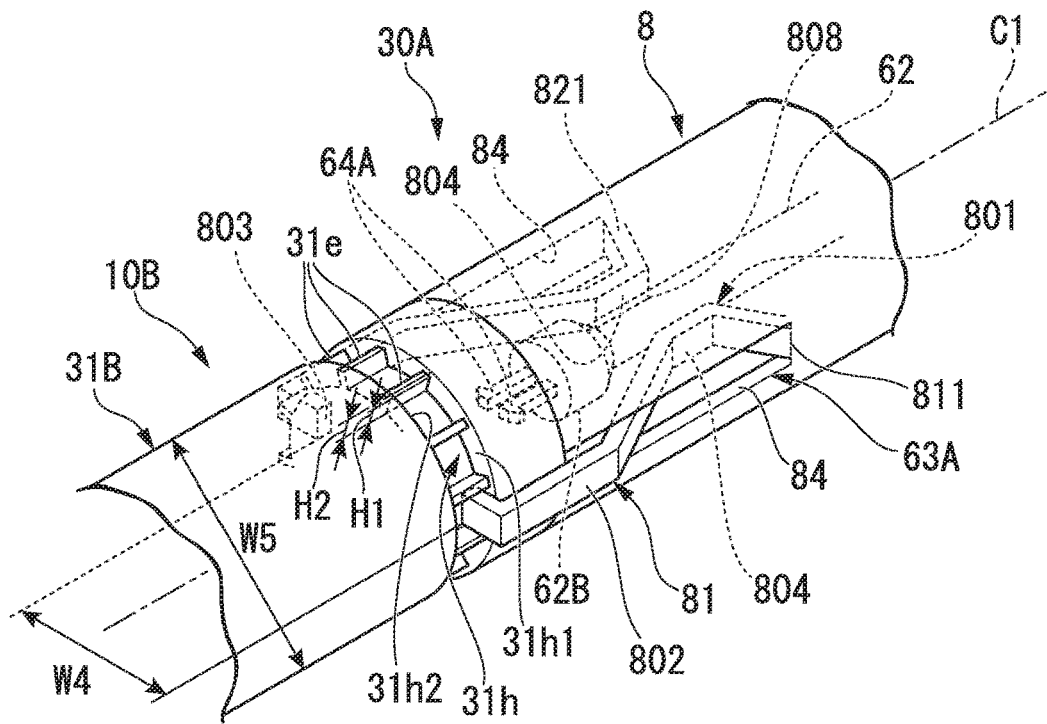
FIG. 20A is a perspective view showing an operation for attaching a clip unit to the applicator according to the present modification.
Figure 20B:
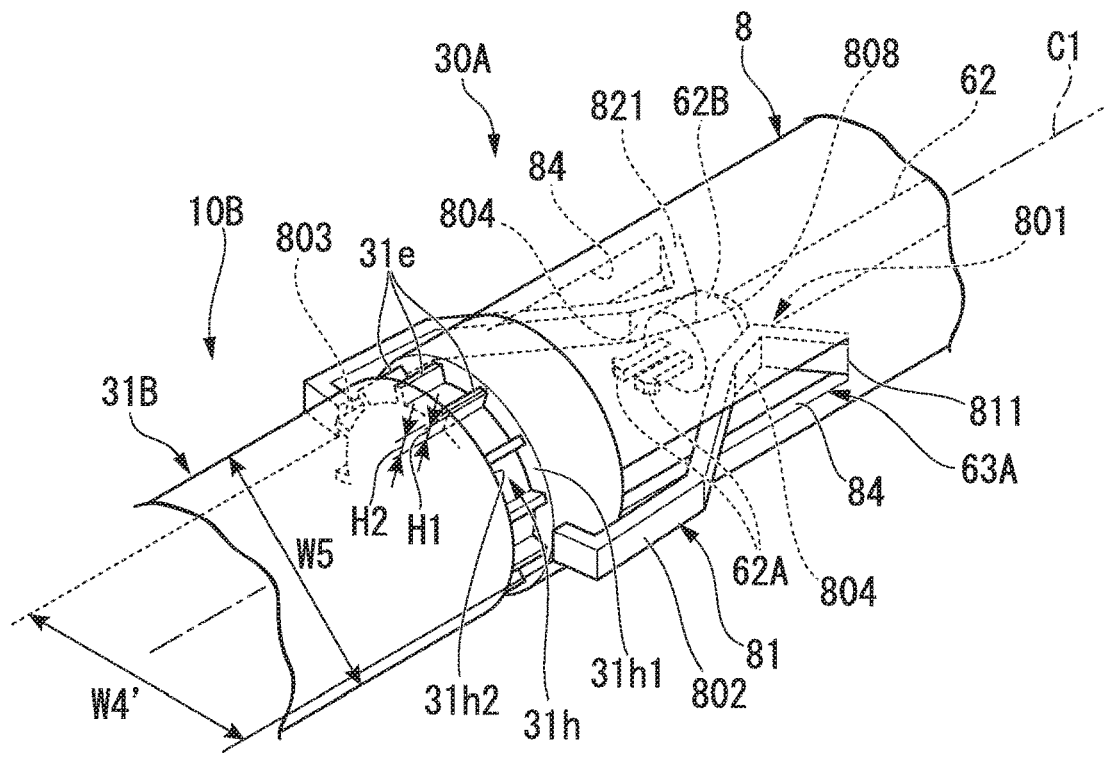
FIG. 20B is a perspective view showing an operation for separating the clip unit from the applicator according to the present modification.

Next, the applicator 30A according to the present modification will be described with reference to FIG. 19, FIG. 20A, and FIG. 20b. FIG. 19 is a lateral view showing the engaged state of the clip 10B and the applicator 30A according to the present modification. FIG. 20A is a perspective view showing the engaged state of the clip 10B and the applicator 30A. FIG. 20B is a perspective view showing that the engaged state of the clip 10B and the applicator 30A is released.

As shown in FIG. 20A, the applicator 30B according to the present modification has an elongated flexible tubular sheath 66 (not shown), and a distal tube 8 fixed at the distal end portion of the sheath 66. The distal tube 8 has a tubular shape with an inner diameter and an outer diameter substantially same as that of the sheath 66. The distal tube 8 has an engaging means 63 including a first leg 81 and a second leg 82.

As shown in FIG. 20A and FIG. 20B, the first leg 81 and the second leg 82 are integrally formed with the distal tube 8 at opposite positions on the circumference of the distal tube 8. A pair of slits 84 are formed to extend from the distal end side toward the proximal end side of the distal tube 8 along the longitudinal direction (axis C1) at opposite positions on the circumference of the distal tube 8. Proximal ends 811, 821 of the first leg 81 and the second leg 82 are connected to the proximal ends of the pair of slits 84, respectively. The first leg 81 and the second leg 82 have same shapes and disposed in symmetrical positions with respect to the longitudinal axis (axis C1).

The first leg 81 and the second leg 82 have elongated plate shapes, proximal ends 811, 821 are fixed to the distal tube 8, and engaging claws 803 are formed at the distal end side as free ends, respectively. Accordingly, the first leg 81 and the second leg 82 are configured to be deformable inwardly or outwardly in the radial direction of the distal tube 8 such that the pair of engaging claws are movable in a direction separating from or approaching the longitudinal direction (axis C1), respectively. The first leg 81 and the second leg 82 are bent at several points along the longitudinal direction. Each of the first leg 81 and the second leg 82 has an inward-protruding portion 801, an outer-parallel portion 802, and the engaging claw 803.

In the first leg 81 and the second leg 82, the inward-protruding portion 801 is formed to protrude inwardly in the radial direction of the distal tube 8 from the proximal ends 811, 821 of the first leg 81 and second leg 82, respectively. In the inward-protruding portion 801, inner-parallel portions 804 are formed by bending the first leg 81 and the second leg 82 at a position at which the distance between the first leg 81 and the second leg 82 is the shortest since the first leg 81 and the second leg 82 protrudes inwardly to approach each other, wherein the inner-parallel portions 804 are formed to parallelly extend from the position described above toward the distal end side, and wherein the first leg 81 and the second leg 82 are bent at the distal ends of the inner-parallel portions 804 so as to incline outwardly in the radial direction of the distal tube 8.

The outer-parallel portions 802 are positioned more distally than the inward-protruding portions 801. The outer-parallel portions 802 are formed to extend along the longitudinal axis so as to be parallel with each other at positions more outward than the outer circumferential surface of the distal tube 8. The engaging claws 803 are formed by inwardly bending the first leg 81 and the second leg 82 at the distal ends of the outer-parallel portions 802 by substantially 90 degrees respectively such that the engaging claws 83 extend to approach each other. The engaging claws 803 are formed to have suitable inward protrusion amounts from the outer-parallel portions 802 such that the engaging claws 803 can enter the outer-groove portions 31h formed on the outer circumferential surface of the pressing tube 31B.

The first leg 81 and the second leg 82 have the smallest distance at the inner-parallel portions 804 respectively. The part at the inner-parallel portions 804 of the first leg 81 and the second leg 82 is defined as a narrow portion 808. As shown in FIG. 20A and FIG. 20b, the narrow portion 808 is formed to have a gap through which the operation wire 62 can be freely inserted. The narrow portion 808 is formed to be narrower than the fixation portion 62B provided at the distal end side of the operation wire 62.

As shown in FIG. 19 and FIG. 20A, according to the applicator 30A of the present modification, the first leg 81 and the second leg 82 of the engaging means 63 are formed on the outer circumferential surface of the distal tube 8. In the present modification, the width between the pair of the engaging claws 803 of the first leg 81 and the second leg 82 in the natural state is set to be equal to or smaller than the outer diameter of the pressing tube 31B. The first leg and the second leg 82 may be biased inwardly in the radial direction of the distal tube 8 by an elastic member (not shown).

In the present modification, the operator can move the applicator 30A toward the clip 10B along the longitudinal axis to move the pair of engaging claws 803 toward the distal end side along the outer circumferential surface of the pressing tube 31B.

As shown in FIG. 20A, the width W4 between the pair of engaging claws 803 of the first leg 81 and the second leg 82 satisfies the Equation 2 shown as below. In the present modification, the pressing tube 31B has an outer diameter W5, the plurality of ribs 31e have the height H2, and the outer-groove portion 31h has a depth H1.

$$W4 < W5 - 2*(H1-H2)$$ [Equation 2]

Accordingly, as shown in FIG. 19 and FIG. 20A, when the pair of engaging claws 803 moves distally along the longitudinal axis and reach the outer-groove portion 31h formed on the outer circumferential surface of the pressing tube 31B, in the same manner as in the embodiment described above, the pair of engaging claws 803 enter the space formed between the plurality of ribs 31e in the outer-groove portion 31h.

In this state, the pair of engaging claws 803 can contact the proximal wall 31h1 of the outer-groove portion 31h at an opposite position with respect to the proximal wall 31h1. Accordingly, in the longitudinal direction, the movement of the pressing tube 31B relative to the distal tube 8 and the sheath 66 according to the present modification is restricted, and the separation of the clip 10B and the applicator 30A is restricted. In other words, when the pair of engaging claws 803 contact and engage with the proximal wall of the outer-groove portion 31h, the engaged state of the clip 10B and the applicator 30A are maintained.

On the other hand, when the pair of engaging claws 803 enter the space S formed between any two adjacent ribs 31e among the plurality of ribs 31e formed in the outer-groove portion 31h, in the circumferential direction about the longitudinal axis, each of the pair of engaging claws 803 is sandwiched by the two adjacent ribs 31e. In this state, the rotation of the pair of engaging claws 803 in the circumferential direction about the longitudinal axis is restricted by the ribs 31e.

At this time, as shown in FIG. 20A, the pair of hooks 62A and the fixation portion 62B provided at the distal end side of the operation wire 62 is positioned more distally than the narrow portion 808 in the distal tube 8. Afterwards, in the same manner as in the embodiment described above, the operator can push the slider 102 of the operation portion 100 toward the distal end side to engage the operation wire 62 with the arm member 11 of the clip 10B.

According to the present modification, in the state in which the first leg 81 and the second leg 82 of the distal tube 8 are engaged with the outer-groove portion 31h of the pressing tube 31B, and the operation wire 62 is engaged with the arm member 11, in the same manner as in the first embodiment, the operator can operate the operation portion 100 (not shown) to rotate the sheath 66 and transmit the rotation operation force applied to the sheath 66 to the pressing tube 31B and the arm member 11. The operator can operate the slider 102 of the operation portion 100 to advance and retract to advance and retract the arm member 11 while transferring the arm member 11 between the open configuration and the close configuration.

Accordingly, in the same manner as in the first embodiment, the operator can treat the target tissue by using the medical instrument (not shown) configured by attaching the clip 10B to the applicator 30A.

During the process of the treatment, together with the advancement and retraction of the arm member 11, the movement of the pressing tube 31B to make the pressing tube 31B to separate from the applicator 30A (the sheath 66 or the distal tube 8) is restricted by the engagement between the first leg 81, the second leg 82 and the outer-groove portion 31h.

When the treatment to the target tissue is finished, in the same manner as in the first embodiment, the operator can release the engagement of operation wire 62 and the arm member 11. As shown in FIG. 20B, the operator can operate the slider 102 of the operation portion 100 (not shown) to separate the clip 10B and the applicator 30A and leave the clip 10B only in the body. More specifically, as shown in FIG. 20B, the operator can retracts the slider 102 (not shown) toward the proximal end side to make the fixation portion 62B disposed at the distal end portion of the operation wire 62 to contact the distal end of the pair of inner-parallel portions 804. As described above, since the width of the fixation portion 62B is larger than the width of the narrow portion 808, due to the retraction operation by the operator to further retract the operation wire 62 toward the proximal end side, the fixation portion 62B engages with and presses the pair of inner-parallel portions 804. As a result, the first leg 81 and the second leg 82 including the engaging claws 803 and the outer-parallel portions 802 are elastically deformed to rotate outwardly in the radial direction of the distal tube 8. Accordingly, as shown in FIG. 20B, the width W4 between the pair of engaging claws 803 changes to a bigger value W4', and the pair of engaging claws 803 are separated from the outer-groove portion 31h of the pressing tube 31B. As a result, the engagement of the applicator 30A and the clip 10B is released and only the clip 10B holding the target tissue is indwelled in the body.

Third Modification

Figure 21A:
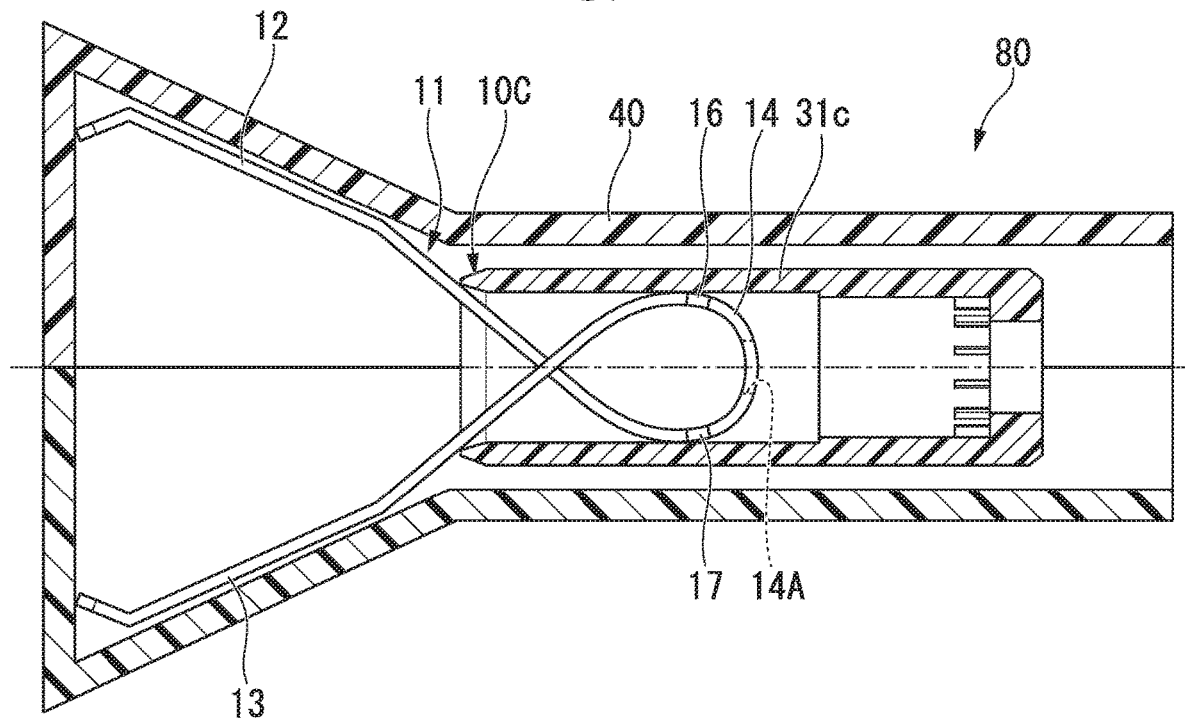
FIG. 21A a partial cross-sectional view in a lateral view schematically showing a configuration of a clip unit according to a third modification of the present embodiment.
Figure 21B:
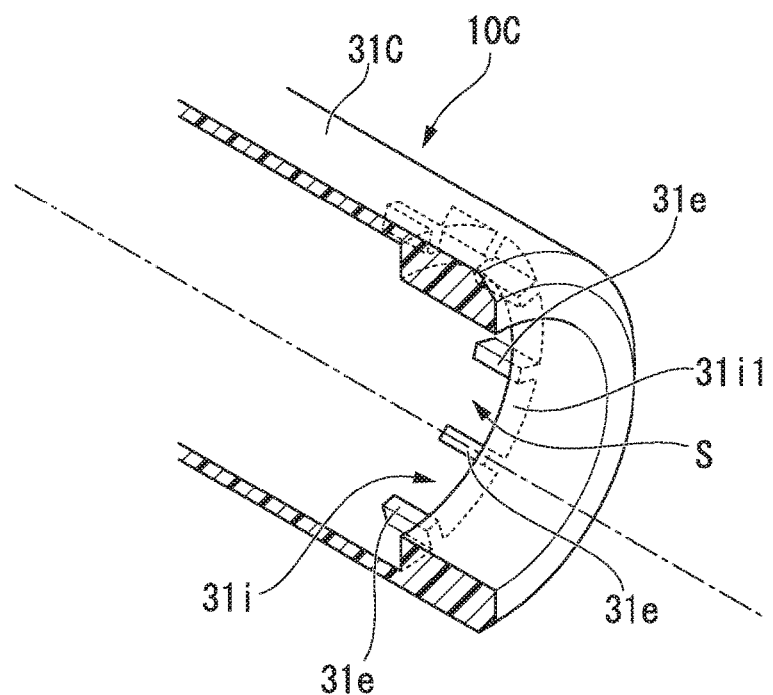
FIG. 21B is a perspective view schematically showing the configuration of the clip unit according to the present modification.

Next, a third modification of the present embodiment will be described with reference to FIG. 21A and FIG. 21B. In the first embodiment described above, it is possible to restrict the movement of the pressing tube 31 for preventing the separation of the pressing tube 31 from the sheath 66 (applicator 30) only if the pair of engaging fingers 63A of the engaging means 63 of the applicator 30 are engaged with the proximal wall (first surface) 31f1 of the inner-groove portion 31f formed in the pressing tube 31. Accordingly, the distal wall 31f2 of the inner-groove portion 31f formed in the pressing tube 31 is not an essential configuration of the present invention.

The configuration of a pressing tube 31C according to the present modification is different from that of the pressing tube 31 according to the first embodiment. Specifically, the pressing tube 31C according to the present modification has a step portion 31i instead of the inner-groove portion 31f according to the first embodiment. As shown in FIG. 21B, the step portion 31i is formed to have a proximal wall (first surface) 31i1 for engaging with the pair of engaging fingers 63A of the engaging means 63. The step portion 31i1 has the plurality of ribs 31e formed at even intervals in the circumferential direction about the longitudinal axis (axis C1). On the other hand, at the more distal side than the plurality of ribs 31e formed in the step portion 31i1, a configuration similar with the distal wall 31f2 of the pressing tube 31 according to the first embodiment is not provided.

According to the present modification, each of the pair of engaging fingers 63A only has to be suitably sandwiched by the two adjacent ribs 31e to restrict the movement in the circumferential direction about the longitudinal axis, the configurations of the step portion 31i and the plurality ribs 31e are not particularly limited.

The first embodiment and various modifications of the first embodiment of the present invention are described. According to the medical instrument according to the modification of the present embodiment, as same as the medical instrument 1 according to the first embodiment, when the operator attaches the clip to the applicator, in the circumferential direction about the longitudinal axis, it is not necessary to match the orientations of the applicator and the clip, the operations of the operator can be simplified.

According to the medical instrument according to the present embodiment and the various modifications, in the state in which the sheath and the pressing tube are fixed with each other, that is, the relative positional relationship between the sheath and the pressing tube is fixed, the rotation operation force of rotating the sheath by the operator can be applied to the pressing tube so as to rotate the clip. In other words, during this process, it is possible to prevent the idling rotation of the pressing tube.

Technical scope of the present invention is not limited to the embodiments and the modifications described above. Additions, omissions, substitutions and other changes in the structure are possible without departing from the spirit of the present invention.

Specifically, for example, the clip 10A having the window portion 31g according to the first modification, and the applicator 30 according to the first embodiment or the applicator 30A according to the second modification may be used in a combination. Furthermore, in the medical instrument according to the present embodiment and various modifications, the configuration example of providing the engaging means in the applicator as the engaged portion and providing the inner-groove portion or the outer-groove portion in the clip as the engaging portion is described. However, the present invention is not limited thereto. For example, the groove portion may be formed over the whole circumference of the inner circumferential surface or the outer circumferential surface of the sheath at the distal end side of the applicator, and the engaging means for engaging with the groove portion may be formed in the small-diameter portion at the proximal end side of the clip. According to the medical instrument having such a configuration, the same effects as that of the medical instrument according to the present embodiment and various modifications can be achieved.

For example, the example of the pair of engaging fingers 63A which rotate inwardly in the radial direction about the axis (not shown) as the rotation center is described; however, the pair of engaging fingers 63A may be configured to make the distal ends to move inwardly in the radial direction due to the elastic deformation of the pair of engaging fingers 63A.

Second Embodiment

Figure 22:
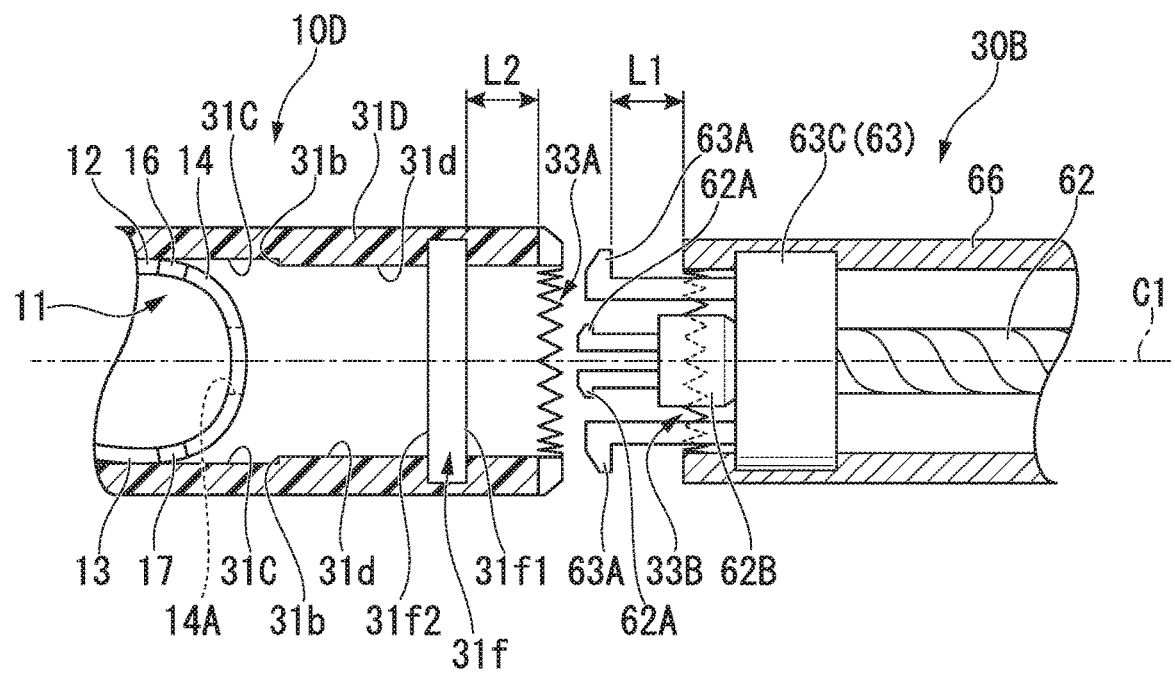
FIG. 22 is a partial cross-sectional view in a lateral view schematically showing configurations of a clip unit and an applicator according to a second embodiment of the present invention.
Figure 23:
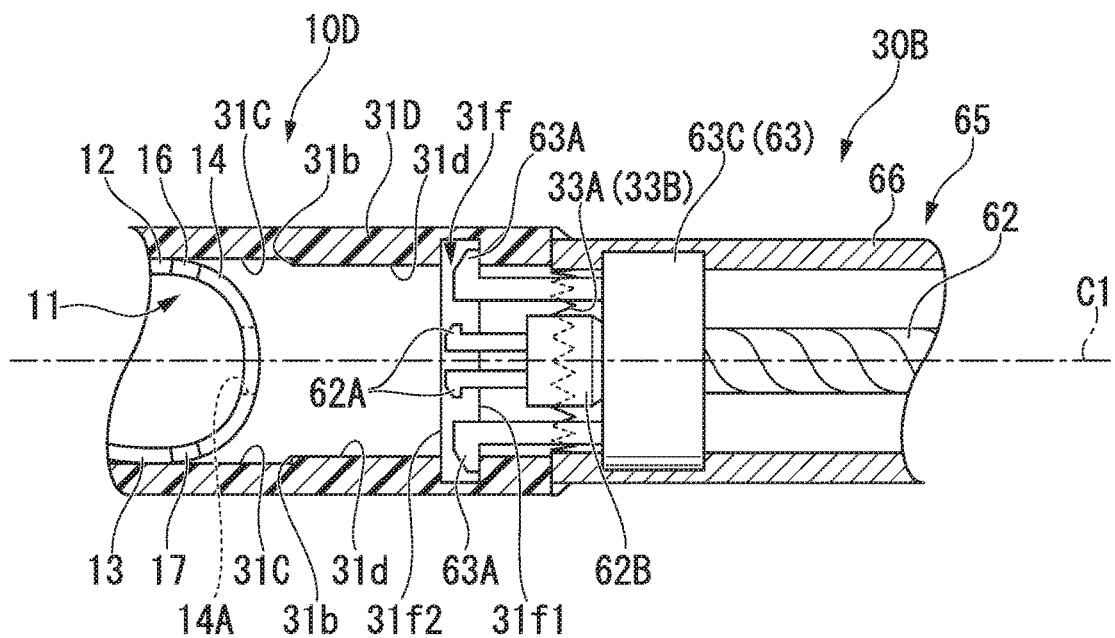
FIG. 23 is a partial cross-sectional view in a lateral view schematically showing a state in which the clip unit and the applicator according to the present embodiment are engaged with each other.
Figure 24:
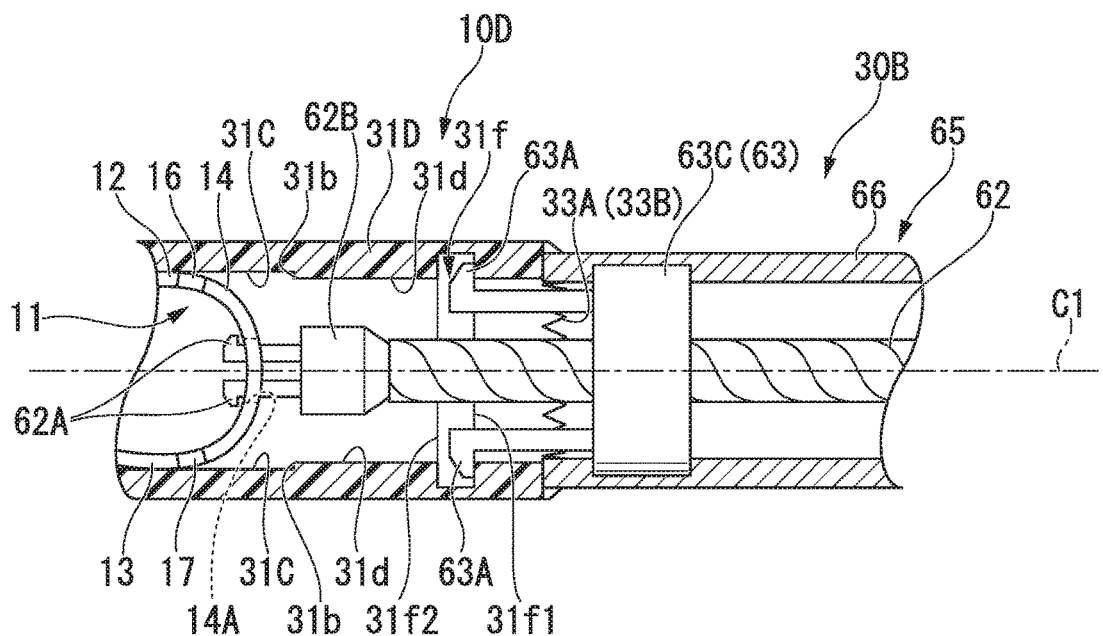
FIG. 24 is a partial cross-sectional view in a lateral view schematically showing the state in which the clip unit and the applicator according to the present embodiment are engaged with each other.

Next, a second embodiment of the present invention will be described with reference to FIG. 22 to FIG. 24. FIG. 22 is a view showing the configurations of an applicator 30B and a clip 10D according to the present embodiment. FIG. 23 is a view showing the engaged state of the applicator 30B and the clip 10D. FIG. 24 is a view showing the engaged state of the operation wire 62 and the arm member 11 of the clip 10D.

As shown in FIG. 22, the clip 10D according to the present embodiment is different from the clip 10 according to the first embodiment in the following aspects. Specifically, in the pressing tube 31D of the clip 10D according to the present embodiment, the plurality of ribs 31e are not formed in the inner-groove portion 31f formed over the whole circumference of the inner circumferential surface of the small-diameter portion 31d. The pressing tube 31D is formed to have a first zigzag portion 33A which is formed from a plurality of protrusions continuously formed in saw tooth shapes, and the first zigzag portion 33A is formed in the circumferential direction about the longitudinal axis (axis C1) over the whole circumference of the proximal surface of the pressing tube 31D. In the present embodiment, the plurality of protrusions in the first zigzag portion 33A are formed to protrude from the proximal end surface of the pressing tube 31D toward the proximal end side along the longitudinal axis (axis c1).

As shown in FIG. 22, in the applicator 30B according to the present embodiment, the cover 63C of the engaging means 63 is fixed on the inner circumferential surface of the sheath 66. The engaging means 63 has the pair of engaging fingers 63A which can engage with the inner-groove portion 31f of the pressing tube 31D. In the present embodiment, since the width W3 of the pair of engaging fingers 63A in the radial direction is set to be larger than the width W1 of the small-diameter portion 31d of the pressing tube 31D, in the same manner as in the first embodiment, the pair of engaging fingers 63A can enter the inner-groove portion 31f of the pressing tube 31D and engage with the inner-groove portion 31f.

In the present embodiment, for example, if the width W3 of the pair of engaging fingers 63A is set to be larger than the width W2 of the inner-groove portion 31f, the pair of engaging fingers 63A can be more definitely engaged with the inner-groove portion 31f. Furthermore, the pair of engaging fingers 63A of the engaging means 63 may be biased outwardly in the radial direction by an elastic member (not shown), that is, the direction in which the pair of engaging fingers 63A separate from each other.

As shown in FIG. 22, in the sheath 66 of the applicator 30B, corresponding to the first zigzag portion 33A described above, a second zigzag portion 33B is formed from a plurality of protrusions continuously formed in saw tooth shapes, and the second zigzag portion 33B is formed in the circumferential direction about the longitudinal axis (axis C1) over the whole circumference of the distal end surface of the sheath 66 of the applicator 30B. In the present embodiment, the plurality of protrusions in the second zigzag portion 33B are formed to protrude from the distal end surface toward the distal end side along the longitudinal direction (axis C1). In the present embodiment, the first zigzag portion 33A and the second zigzag portion 33B may be formed to have the same shape and the same dimensions so as to be capable of being tightly engaged with each other.

In the present embodiment, as shown in FIG. 22, in the longitudinal direction (axis C1), a distance 11 from the distal ends of the plurality of protrusions of the second zigzag portion 33B of the applicator 30B to the finger 63A is set to be substantially same as a distance L2 from the proximal end surface of the clip 10D to the proximal wall 31f1 of the inner-groove portion 31f. Accordingly, as shown in FIG. 23, when the clip 10D and the applicator 30B are engaged with each other, the pair of engaging fingers 63A are engaged with the proximal wall (first surface) 31f1 of the inner-groove portion 31f, and the first zigzag portion 33A is tightly engaged with the second zigzag portion 33B. Here, the phrase "tightly engaged" means that when the first zigzag portion 33A is engaged with the second zigzag portion 33B, there is almost no gap formed between any of the protrusion of the first zigzag portion 33A and the adjacent protrusion of the second zigzag portion 33B. With regard to the protrusion of the second zigzag portion 33B adjacent to the protrusion of the first zigzag portion 33A, the lateral surface contacting the first zigzag portion 33A is defined as the second surface in the engagement of the first zigzag portion 33A and the second zigzag portion 33B.

Due to the manufacturing tolerances and the like, in a case in which a gap is formed between any of the protrusion of the first zigzag portion 33A and the adjacent protrusion of the second zigzag portion 33B, if the rotation operation force by the operator can be suitably transmitted to the pressing tube 31D, such tolerances are acceptable in the present embodiment.

According to the configurations of the clip 10D and the applicator 30B according to the present embodiment, as shown in FIG. 23, the operator can connect (engage) the sheath 66 with the pressing tube 31D by moving the applicator 30B toward the clip 10D in the longitudinal direction. At this time, the engagement of the pair of engaging fingers 63A and the inner-groove portion 31f, and the engagement of the first zigzag portion 33A and the second zigzag portion 33B can be realized at almost the same time. In the same manner as in the first embodiment, the movement of the pressing tube 31D leading to the separation of the pressing tube 31D from the sheath 66 is restricted by engaging the pair of engaging fingers 63A with the inner-groove portion 31f. On the other hand, due to the engagement of the first zigzag portion 33A and the second zigzag portion 33b, the operator can operate the operation portion 100 (not shown) to transmit the rotation operation force for rotating the sheath 66 to the pressing tube 31D of the clip 10D.

In the state in which the sheath 66 is connected with the pressing tube 31, as shown in FIG. 24, the operator can operate the slider 102 of the operation portion 100 (not shown) to move the operation wire 62 toward the distal end side so as to connect (engage) the operation wire 62 with the arm member 11. In this state, when the operator operates the operation portion 100 to rotate the sheath 66, the rotation operation force is applied to the pressing tube 31D so as to rotate both of the pressing tube 31D and the arm member 11 in the circumferential direction about the longitudinal axis.

The first zigzag portion 33A and the second zigzag portion 33B according to the present embodiment only have to be capable of tightly engaging with each other, the shape thereof is not particularly limited. For example, with regard to the plurality of protrusions in the first zigzag portion 33A and the second zigzag portion 33B, the length in the longitudinal direction (axis C1), and the width in the circumferential direction about the longitudinal axis may be suitably changed.

According to the present embodiment, after the operator attaches the clip 10D to the applicator 30B to configured the medical instrument 1 and performs treatment to the target tissue using the medical instrument 1, in the same manner as in the first embodiment, the operator can retract the operation wire 62 to release the engagement of the pair of engaging fingers 63A and the inner-groove portion 31f. Accordingly, only the clip 10D is indwelled inside the body while ligating the target tissue.

According to the present embodiment, in the same manner as in the first embodiment, in the engaged state of the sheath 66 and the pressing tube 31D, the operator can rotate the sheath 55 so as to rotate the pressing tube 31D and the arm member 11 for adjusting the orientation of the arm member 11. In this process, the first zigzag portion 33A is engaged with the second zigzag portion 33B such that the idling rotation of the pressing tube 31D can be prevented.

On the other hand, the operator can advance and retract the operation wire 62 to transfer the arm member 11 between the open configuration and the close configuration. Furthermore, when the pair of protrusions 16, 17 provided at the arm member 11 is in the range more distal than the step portion 31b of the pressing tube 31D, the operator can advance and retract the operation wire 62 to repeatedly grasp the target tissue using the arm member 11.

According to the present embodiment, since the inner-groove portion 31f is formed over the whole circumference of the inner circumferential surface of the small-diameter portion 31d of the pressing tube 31D, and the first zigzag portion 33A and the second zigzag portion 33B are formed on the proximal end surface of the pressing tube 31D and the distal end surface of the sheath 66 respectively, during the operation of attaching the clip 10D to the applicator 30B by the operator, it is not necessary to match the relative position between the clip 10D and the applicator 30B in the circumferential direction.

First Modification

Next, various modifications of the present embodiment will be described with reference to FIG. 25A to FIG. 27B.

Figure 25A:
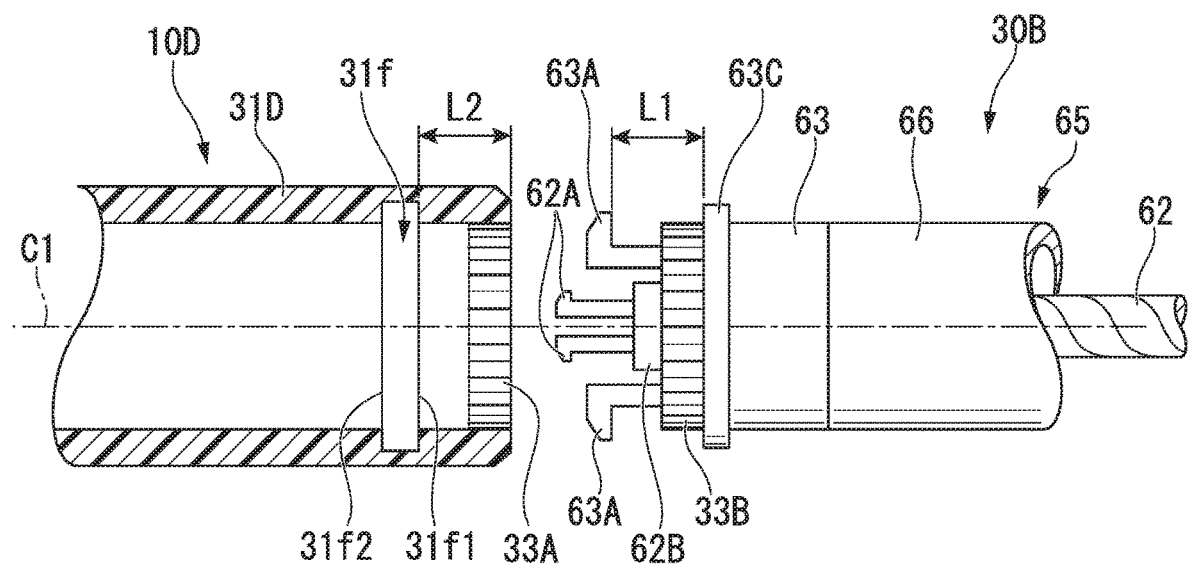
FIG. 25A is a partial cross-sectional view in a lateral view schematically showing configurations of a clip unit and an applicator according to a first modification of the present embodiment.

As shown in FIG. 25A, according to a first modification of the present embodiment, the first zigzag portion 33A is formed over the whole circumference of the inner circumferential surface of the small-diameter portion 31*d* of the pressing tube 31D, and the second zigzag portion 33B is formed over the whole circumference of the outer circumferential surface of the cover 63C of the engaging means 63. In other words, in the pressing tube 31D, the plurality protrusions of the first zigzag portion 33A are formed to protrude inwardly in the radial direction from the inner circumferential surface of the pressing tube 31D. On the other hand, the plurality of protrusions of the second zigzag portion 33B are formed to protrude outwardly in the radial direction from the outer circumferential surface of the cover 63C of the engaging means 63.

Figure 25B:
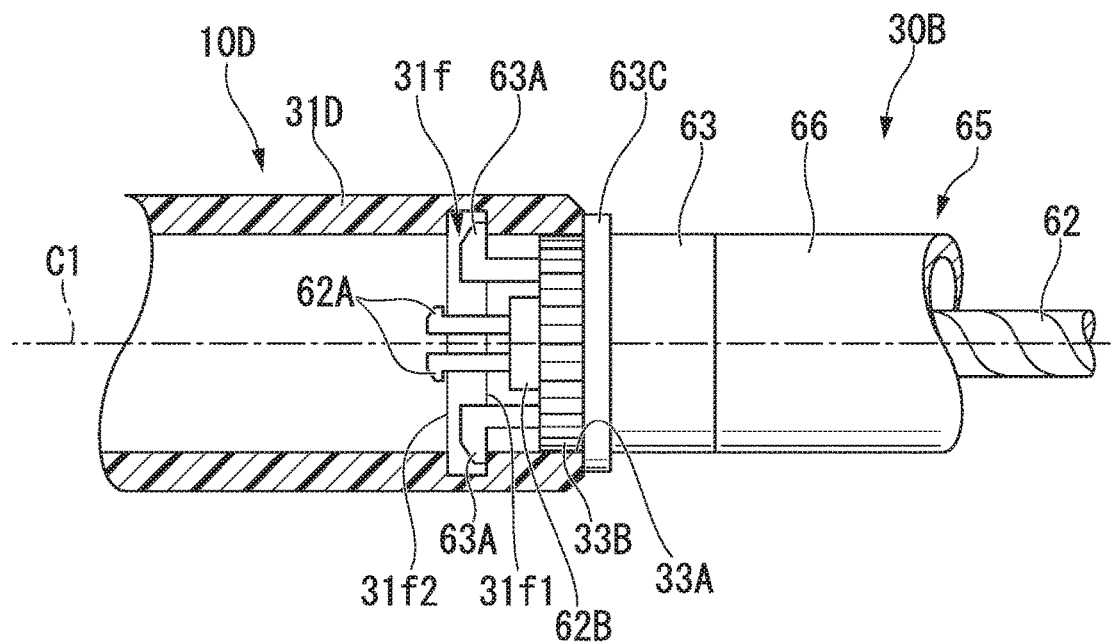
FIG. 25B is a partial cross-sectional view in a lateral view schematically showing a state in which the clip unit and the applicator according to the present modification are engaged with each other.

In the present modification, the insertion portion 65 of the applicator 30 including the engaging means 63 and the sheath 66 has the dimension suitable for being inserted into the pressing tube 31D. As shown in FIG. 25A, in the longitudinal direction (axis C1), the distance L1 from the proximal end surface of the second zigzag portion 33B of the applicator 30B is substantially the same as the distance L2 from the proximal end surface of the pressing tube 31D to the proximal wall 31*f*1 of the inner-groove portion 31*f*. Accordingly, when the operator moves the applicator 30B toward the clip 10D, as shown in FIG. 25B, the pair of engaging fingers 63A are engaged with the proximal wall 31*f*1 of the inner-groove portion 31*f*1 in the pressing tube 31D, and the first zigzag portion 33A is engaged with the second zigzag portion 33B. In this state, as same as the second embodiment, the operator can operate the operation portion 100 (not shown) to rotate the sheath 66 so as to rotate the pressing tube 31D due to the engagement of the first zigzag portion 33A and the second zigzag portion 33B.

Second Modification

Figure 26A:
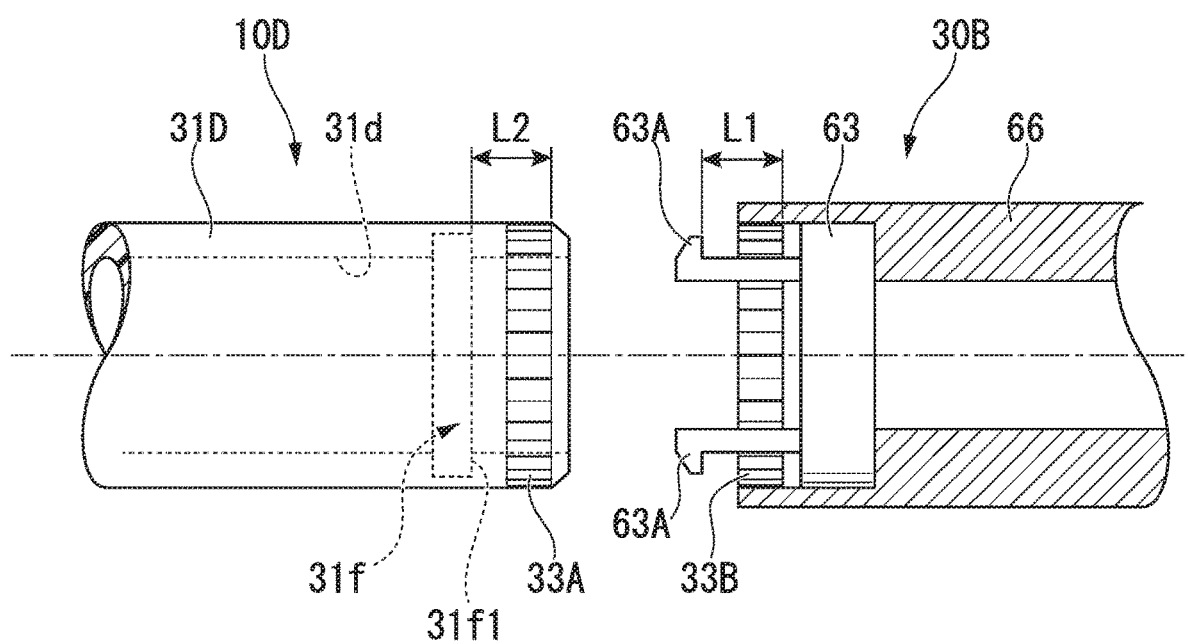
FIG. 26A is a partial cross-sectional view in a lateral view schematically showing configurations of a clip unit and an applicator according to a second modification of the present embodiment.
Figure 26B:
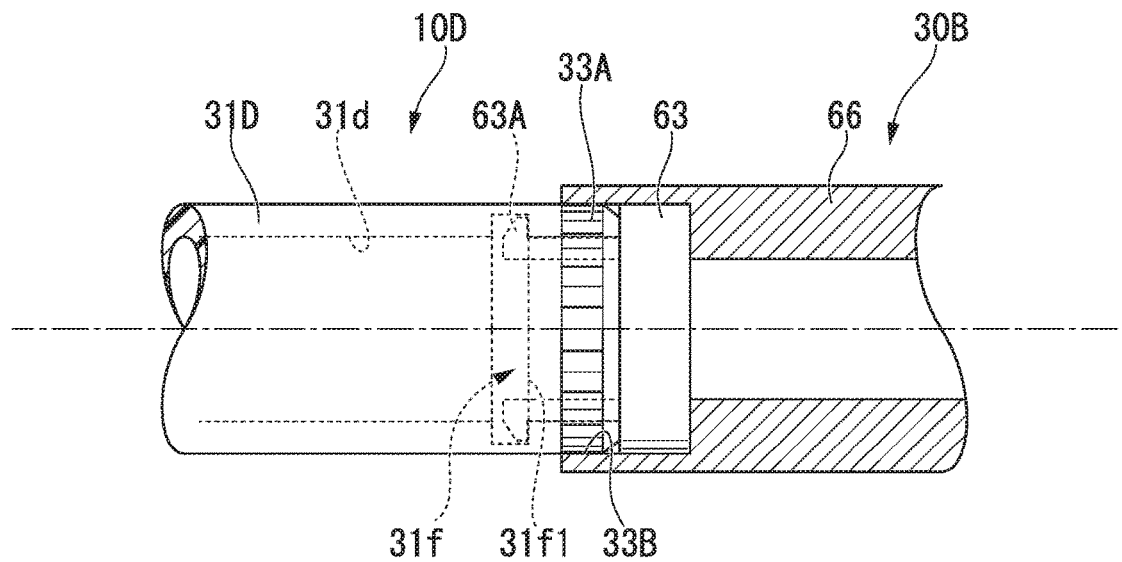
FIG. 26B is a partial cross-sectional view in a lateral view schematically showing a state in which the clip unit and the applicator according to the present modification are engaged with each other.

As shown in FIG. 26A and FIG. 26B, in the clip 10D according to the second modification of the present embodiment, the first zigzag portion 33A is formed on the outer circumferential surface at the proximal end side of the pressing tube 31D. On the other hand, the second zigzag portion 33B is formed on the inner circumferential surface at the distal end side of the sheath 66 in the applicator 30B. The engaging means 63 having the pair of engaging fingers 63A is fixed to the inner circumferential surface of the sheath 66 of the applicator 30B.

In the present modification, the distal end portion of the sheath 66 of the applicator 30 has the inner diameter so as to be able to accommodate at least part of the small-diameter portion 31*d* at the proximal end side of the pressing tube 31D. As shown in FIG. 26A, in the longitudinal direction (axis C1), the distance L1 from the proximal end of the second zigzag portion 33B of the applicator 30B to the engaging finger 63A is substantially the same as the distance L2 from the proximal end surface of the first zigzag portion 33A of the pressing tube 31D to the proximal wall 31*f*1 of the inner-groove portion 31*f*. Accordingly, when the operator moves the applicator 30B toward the clip 10D, as shown in FIG. 26B, the pair of engaging fingers 63A are engaged with the proximal wall 31*f*1 of the inner-groove portion 31*f* in the pressing tube 31D, and the first zigzag portion 33A is engaged with the second zigzag portion 33B. In this state, as same as the second embodiment, the operator operates the operation portion 100 (not shown) to rotate the sheath 66 so as to rotate the pressing tube 31D due to the engagement of the first zigzag portion 33A and the second zigzag portion 33B.

Third Modification

Figure 27A:
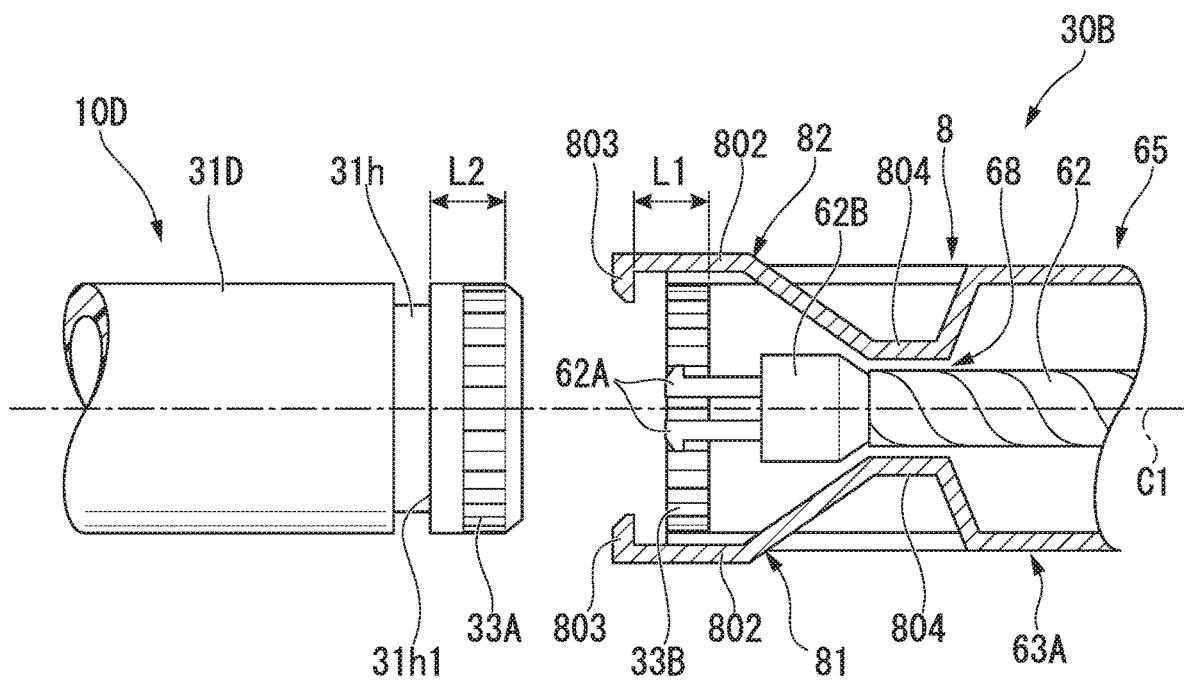
FIG. 27A is a partial cross-sectional view in a lateral view schematically showing configurations of a clip unit and an applicator according to a third modification of the present embodiment.

As shown in FIG. 27A, the outer-groove portion 31*h* and the first zigzag portion 33A are formed on the outer circumferential surface at the proximal end side of the pressing tube 31*d* of the clip 10D according to a third modification of the present embodiment. On the other hand, the second zigzag portion 33B is formed on the inner circumferential surface of the distal tube 8 fixed to the distal end side of the sheath 66 of the applicator 30B. The distal tube 8 in the applicator 30B according to the present modification has the engaging means 63 including the first leg 81 and the second leg 82. As shown in FIG. 27A, the pair of outer-parallel portions 802 and engaging claws 803 are disposed more outwardly than the outer circumferential surface of the distal tube 8 (applicator 30B).

Figure 27B:
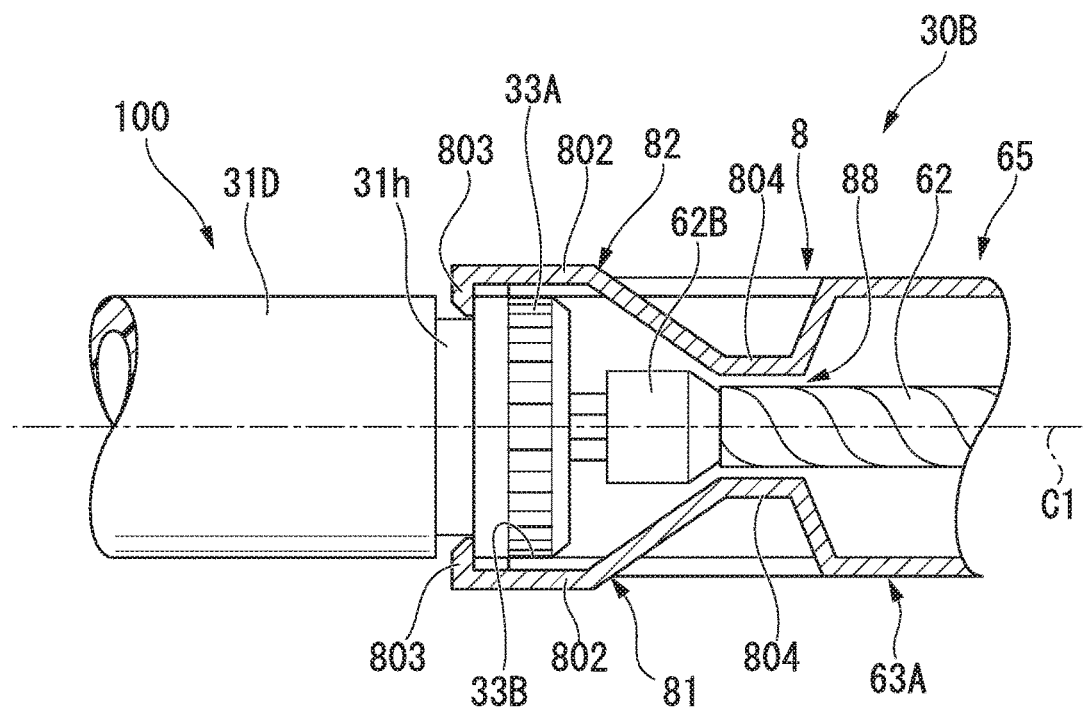
FIG. 27B is a partial cross-sectional view in a lateral view schematically showing a state in which the clip unit and the applicator according to the present modification are engaged with each other.

As shown in FIG. 27A, in the applicator 30B according to the present modification, the distance L1 from the proximal end surface of the second zigzag portion 33B to the engaging claw 803 is substantially the same as the distance L2 from the first zigzag portion 33A formed on the outer circumferential surface of the pressing tube 31D to the proximal wall 31*h*1 of the outer-groove portion 31*h*. Accordingly, when the operator moves the applicator 30B toward the clip 10D, as shown in FIG. 27B, the first leg 81 and the second leg 82 are elastically deformed and engaged with the outer-groove portion 31*h* of the pressing tube 31D so as to connect the applicator 30B with the clip 10D. At this time, the pair of engaging claws 803 are engaged with the proximal wall 31*h*1 of the outer-groove portion 31*h*, and the first zigzag portion 33A is engaged with the second zigzag portion 33B. In this state, in the same manner as in the modifications described above, the operator can operate the operation portion 100 (not shown) to rotate the sheath 66 so as to rotate the pressing tube 31D due to the engagement of the first zigzag portion 33A and the second zigzag portion 33B.

The second embodiment and various modifications of the present embodiment are described. According to the present embodiment and the modifications, in the pressing tube, the plurality of ribs are not formed in the inner-groove portion or the outer-groove portion. Instead, by forming the first zigzag portion and the second zigzag portion, the same effects as those of the first embodiment can be achieved.

Third Embodiment

Figure 28:
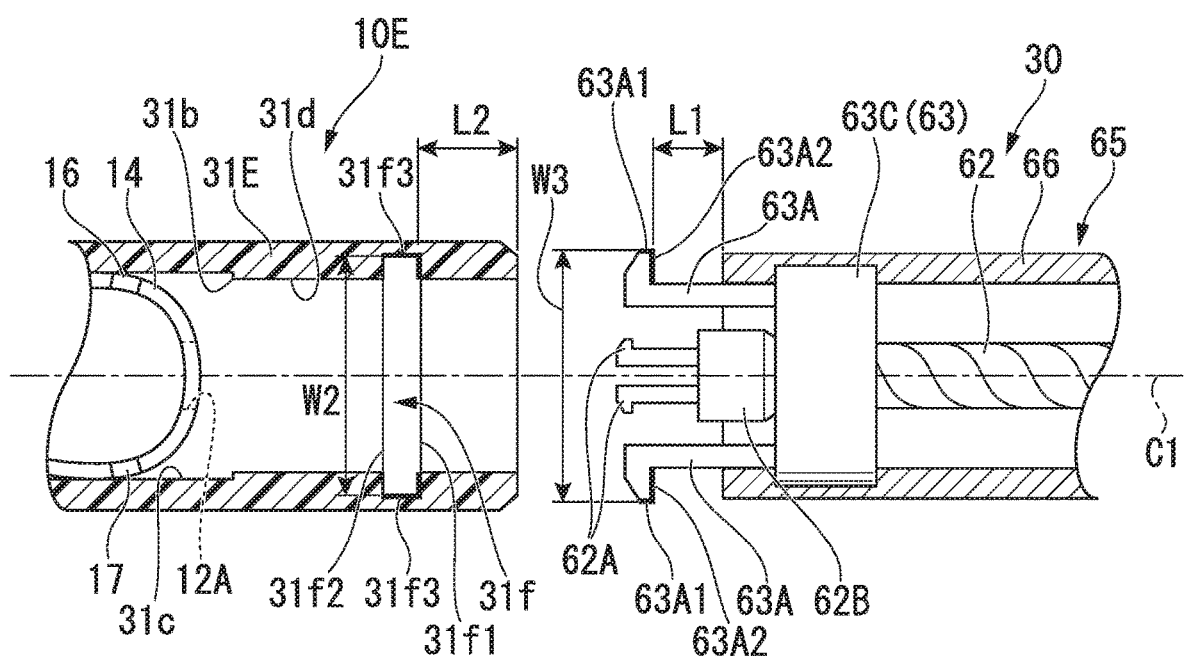
FIG. 28 is a partial cross-sectional view in a lateral view schematically showing configurations of a clip unit and an applicator according to a third embodiment of the present invention.
Figure 29:
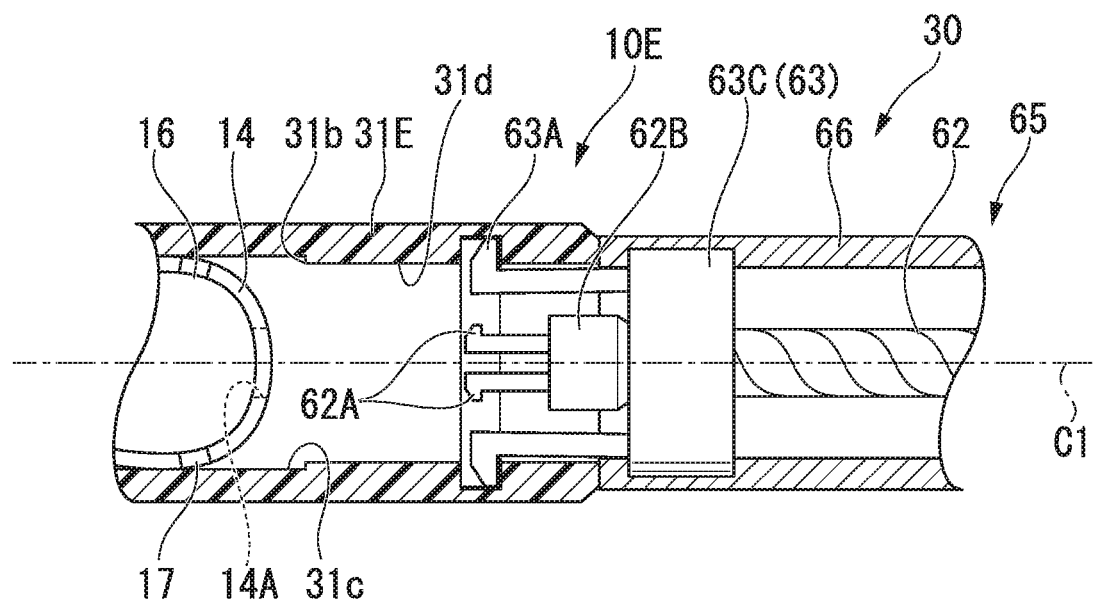
FIG. 29 is a partial cross-sectional view in a lateral view schematically showing a state in which the clip unit and the applicator according to the present embodiment are engaged with each other.
Figure 30:
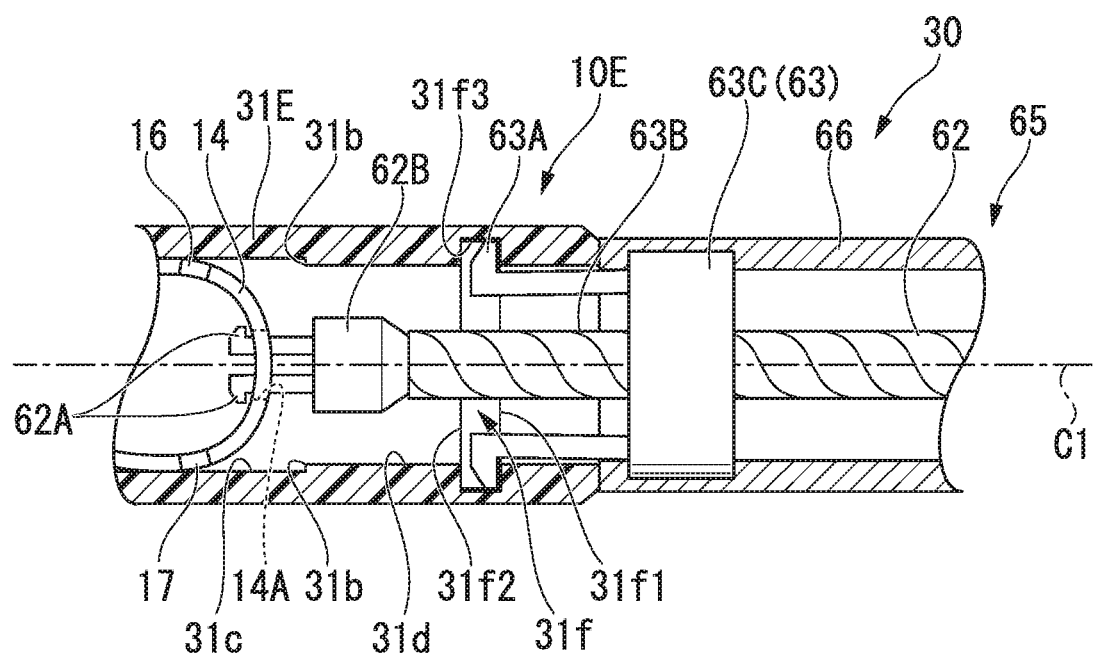
FIG. 30 is a partial cross-sectional view in a lateral view schematically showing the state in which the clip unit and the applicator according to the present embodiment are engaged with each other.
Figure 31:
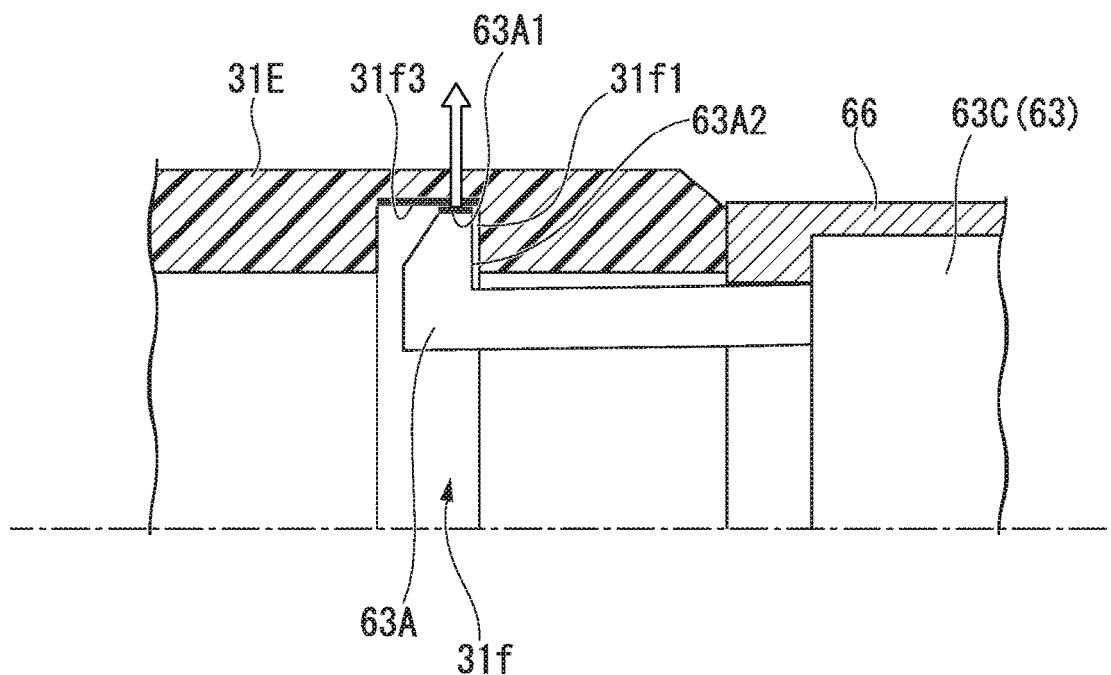
FIG. 31 is an enlarged cross-sectional view schematically showing the state in which the clip unit and the applicator according to the present embodiment are engaged with each other.
Figure 32:
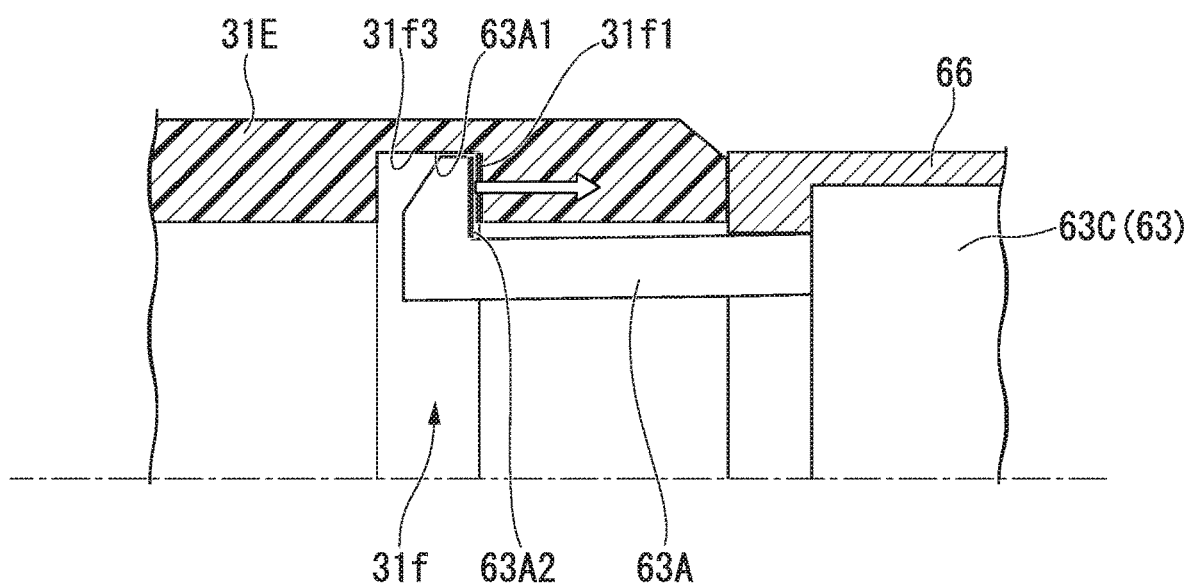
FIG. 32 is an enlarged cross-sectional view schematically showing the state in which the clip unit and the applicator according to the present embodiment are engaged with each other.

Next, a third embodiment of the present invention will be described with reference to FIG. 28 to FIG. 32. FIG. 28 is a view showing the configurations of the applicator 30 and a clip 10E according to the present embodiment. FIG. 29 and FIG. 30 are views showing the operations of attaching the clip 10E to the applicator 30 according to the present embodiment. FIG. 31 and FIG. 32 are partial enlarged views showing the engaged state of the clip 10E and the applicator 30 according to the present embodiment.

As shown in FIG. 28, in the pressing tube 31E of the clip 10E according to the present embodiment, the inner-groove portion 31*f* having the width W2 in the radial direction is formed over the whole circumference of the inner circumferential surface of the small-diameter portion 31*d*. However, in the inner-groove portion 31*f*, the plurality of ribs are not formed. In the inner-groove portion 31*f*, surface processing is performed with respect to at least one of the proximal wall (first surface) 31*f*1 and the inner circumferential surface (second surface) 21*f*3. More specifically, at least one of the proximal wall 31*f*1 and the inner circumferential surface 21*f*3 of the inner-groove portion 31*f* is processed from a smooth surface to a surface having roughness equal to or larger than a predetermined roughness.

In the applicator 30 according to the present embodiment, the engaging means 63 is fixed to the inner circumferential surface at the distal end side of the sheath 66. The engaging means 63 is configured to have the pair of engaging fingers 63A protruding from the distal opening of the sheath 66 in the longitudinal direction (axis C1). The width W3 of the pair of engaging fingers 63A is set to be equal to or larger than the width W2 of the inner-groove portion 31*f*. On the other hand, the distance L1 from the distal end surface of the sheath 66 of the applicator 30 to the surface 63A2 of the engaging finger 63A is substantially the same as the distance L2 from the proximal end surface of the pressing tube 31E of the clip 10E to the proximal wall 31*f*1 of the inner-groove portion 31*f*.

Furthermore, in the present embodiment, the pair of engaging fingers 63A may be biased outwardly in the radial direction or toward the proximal end side in the longitudinal direction (axis C1) by having an elastic member (not shown). Also, the pair of engaging fingers 63A may be biased toward both directions described above.

As shown in FIG. 28, the surface 63A1 and the surface 63A2 in the engaging claw formed at the distal end side of the pair of engaging fingers 63A are processed so as to have the roughness equal to or larger than the predetermined roughness, similarly with the proximal wall 31*f*1 and the inner circumferential surface 31*f*3 of the inner-groove portion 31*f*.

The clip 10E and the applicator 30 according to the present embodiment have the configurations described above, when the operator attaches the clip 10E to the applicator 30, the operator moves the applicator 30 toward the clip 10E. As shown in FIG. 29, since the width W3 of the pair of engaging fingers 63A is larger than the width W1 of the pressing tube 31E, the pair of engaging fingers 63A are elastically deformed and slided inside the small-diameter portion 31*d* toward the distal end side. When the pair of engaging fingers 63A are moved to the position of the inner-groove portion 31*f*, the pair of engaging fingers 63A restore to the original width W3 due to their own elastic restoring force. The width W3 of the pair of engaging fingers 63A are set to be equal to or more than the width W2 of the inner-groove portion 31*f* such that the surface 63A1 comes in contact the inner circumferential surface 31*f*3 of the inner-groove portion 31*f* and the pair of engaging fingers 63A presses the pressing tube 31E outwardly in the radial direction (see FIG. 31). In other words, the pair of engaging fingers 63A applies a pressing force outwardly in the radial direction to the pressing tube 31E. Accordingly, the surfaces 63A1 of the pair of engaging fingers 63A are engaged with the inner circumferential surface 31*f*3 of the inner-groove portion 31*f* in the pressing tube 31E. At the same time, the surfaces 63A2 of the pair of engaging fingers 63A of the applicator 30 are engaged with the proximal wall 31*f*1 of the inner-groove portion 31*f* (see FIG. 32).

Accordingly, as shown in FIG. 29, when the clip 10E is connected with the applicator 30, the pair of engaging fingers 63A and the pressing tube 31E are engaged with each other due to at least one of the engagement between the surface 63A1 and the inner circumferential surface 31*f*3 and the engagement between the surface 63A2 and the proximal wall 31*f*1. The pair of engaging fingers 63A and the pressing tube 31E may be engaged with each other due to both of the engagements described above.

In the state in which the clip 10E is connected with the applicator 30, as shown in FIG. 30, the operator can engage the operation wire 62 with the arm member 11 by pushing the slider 102 of the operation portion 100 (not shown) toward the distal end side.

In this state, when the operator operates the operation portion 100 (not shown) to rotate the sheath 66, the pair of engaging fingers 63A tries to rotate in the circumferential direction relative to the pressing tube 31E. Accordingly, a friction force is generated to stop the relative movement between the engaging finger 63A and the pressing tube 31E, wherein the friction force is generated between the surface 63A1 of the engaging finger 63A and the inner circumferential surface 31*f*3 of the inner-groove portion 31*f*, or between the surface 63A2 of the engaging finger 63A and the proximal wall 31*f*1 of the inner-groove portion 31*f*.

In the present embodiment, since the surface 63A1, the surface 63A2, and the inner circumferential surface 31*f*3 and the proximal wall 31*f*1 of the inner-groove portion 31*f* are formed to have the suitable roughness, the pressing tube 31E can be rotated together with the rotation of the sheath 66 due to the friction force between the engaging finger 63A and the pressing tube 31E. In other words, according to the clip 10E and the applicator 30 according to the present embodiment, the operator can operate the operation portion 100 (not shown) to rotate the sheath 66 while rotating the pressing tube 31E and the arm member 11 together.

FIG. 31 is a view showing the engaged state in which the engaging finger 63A is only engaged with the inner circumferential surface 31*f*3 of the inner-groove portion 31*f* of the pressing tube 31E. FIG. 32 is a view showing the engaged state in which the engaging finger 63A is only engaged with the proximal wall 31*f*1 of the inner-groove portion 31*f* of the pressing tube 31E. In the present embodiment, the rotation operation force generated at the time when the operator rotates the sheath 66 can be transmitted to the pressing tube 31E if the engaging finger 63A and the pressing tube 31E are engaged with each other as same as the engaged state as shown in either of FIG. 31 or FIG. 32. Furthermore, the engaging finger 63A and the pressing tube 31E may be engaged with each other in both of the longitudinal direction (axis C1) and the radial direction.

In the present embodiment, since the operator can transmit the rotation operation force for rotating the sheath 66 to the pressing tube 31E due to the friction force generated between the engaging finger 63A and the pressing tube 31E, same effects as that of the first embodiment can be achieved. In this case, in order to make the engaging finger 63A and the pressing tube 31 to engage with each other more definitely, as described above, it is preferable to provide the elastic member in the engaging means 63 of the applicator 30 so as to bias the pair of engaging fingers 63A outwardly in the radial direction or bias the pair of engaging fingers 63A toward the proximal end side in the longitudinal direction (axis C1).

Several embodiments and modifications of the present invention have been described above; however, the technical scope of the present invention is not limited to the embodiments and the modifications described above. Additions, omissions, substitutions and other changes in the structure are possible without departing from the spirit of the present invention.

In the embodiments and modifications described above, the configuration example of providing the engaging means in the applicator as the engaged portion and providing the inner-groove portion or the outer-groove portion in the clip as the engaging portion is described. However, the present invention is not limited thereto. Specifically, for example, the engaging means having the pair of engaging fingers may be disposed at the proximal end side of the clip, and the groove portion may be formed over the whole circumference of the inner circumferential surface or the outer circumferential surface of the sheath at the distal end side of the applicator.

What is claimed is:

1. A medical instrument, comprising:
    a capsule that is formed in a cylindrical shape and has a longitudinal axis;
    an arm member disposed to protrude from the capsule and configured to be rotatable together with the capsule about the longitudinal axis;
    an operation wire connected to the arm member, the operation wire being separatable from the arm member;
    a sheath configured to accommodate the operation wire; and
    a link configured to connect the sheath with the capsule, the sheath and the capsule being separatable from each other, the link including:
        an engaging portion including a first surface intersecting with the longitudinal axis; and
        an engaged portion configured to protrude in an intersection direction with respect to the longitudinal axis, the engaged portion being movable to an opposite position opposite to the first surface and a position spaced away from the first surface in the intersection direction in spite of a relative position of the capsule with respect to the sheath in a circumferential direction about the longitudinal axis, and the engaged portion being configured to restrict a separation of the capsule with respect to the sheath when the engaged portion is disposed at the opposite position to contact the first surface,
    wherein:
        the capsule is rotatable about the longitudinal axis in response to a rotational force about the longitudinal axis from the sheath when the engaged portion is disposed at the opposite position,
        the arm member, the capsule, and the sheath are configured to rotate about the longitudinal axis in an interlocking manner with respect to the operation wire when the engaged portion is disposed at the opposite position, and
        the operation wire and the arm member are relatively rotatable with respect to each other.

2. The medical instrument according to claim 1, wherein the first surface extends around a whole circumference of the capsule or the sheath.

3. The medical instrument according to claim 1, wherein the engaged portion is provided in the sheath and the engaging portion is formed on an inner peripheral surface or an outer peripheral surface of the capsule.

4. The medical instrument according to claim 1, wherein the engaged portion is provided in the capsule and the engaging portion is formed on an inner peripheral surface or an outer peripheral surface of the sheath.

5. The medical instrument according to claim 1, wherein the link is configured to transmit the rotational force about the longitudinal axis from the sheath to the capsule due to an engagement of the engaging portion and the engaged portion.

6. The medical instrument according to claim 5, wherein:
    the engaging portion includes a second surface which faces in a direction different from that of the first surface, and
    the second surface is configured to contact the engaged portion when the sheath rotates about the longitudinal axis and the engaged portion is positioned at the opposite position such that the rotational force of the sheath is transmitted to the capsule.

7. The medical instrument according to claim 6, wherein:
    the engaging portion includes a groove, and
    the second surface is disposed at a deeper side of the groove than the first surface along a whole circumference of the engaging portion about the longitudinal axis.

8. The medical instrument according to claim 6, wherein the second surface is disposed at a position opposite to the engaged portion in the circumferential direction about the longitudinal axis when the engaged portion is disposed at the opposite position.

9. The medical instrument according to claim 6, wherein:
    wherein the second surface is configured to contact the engaged portion when the engaged portion is disposed at the opposite position, and
    the sheath is configured to transmit the rotational force to the capsule by a frictional force generated between the second surface and the engaged portion when the sheath rotates about the longitudinal axis.

10. The medical instrument according to claim 1, wherein:
    the first surface is configured to contact the engaged portion when the engaged portion is disposed at the opposite position, and
    the sheath is configured to transmit the rotational force to the capsule by a frictional force generated between the first surface and the engaged portion when the sheath rotates about the longitudinal axis.

11. The medical instrument according to claim 1, wherein:
    the engaging portion is provided at a surface of the capsule,
    the engaged portion is provided at a surface of the sheath, the engaged portion being engaged with the engaging portion when the engaged portion is disposed at the opposition opposite position, and
    the rotational force of the sheath is transmitted to the capsule due to an engagement of the engaging portion and the engaged portion.

12. The medical instrument according to claim 11, wherein the engaging portion and the engaged portion are engaged with each other due to a concave structure with a convex structure which can be coupled with each other.

13. The medical instrument according to claim 1, wherein the engaging portion includes a plurality of ribs that protrude in a radial direction and are configured to engage the engaged portion when the sheath is rotated about the longitudinal axis to transmit the rotational force from the sheath to the capsule.

14. A clip unit connected to an applicator, the clip unit and the applicator being separatable from each other, and the applicator having an operation wire configured to be operated by an operator, a sheath configured to accommodate the operation wire, and an engaged portion protruding in an intersection direction intersecting with a central axis of the sheath, comprising:
- a capsule that is formed in a cylindrical shape and has a longitudinal axis, the capsule being connected to the sheath and separatable from the sheath; and
- an arm member disposed to protrude from the capsule, the arm member being connected to the operation wire and separatable from the operation wire, wherein:
- the arm member is configured to be integrally rotatable with the capsule about the longitudinal axis,
- the capsule includes an engaging portion with a first surface intersecting with the longitudinal axis,
- the first surface can face the engaged portion in spite of a relative position of the capsule with respect to the sheath in a circumferential direction about the longitudinal axis, and the first surface can restrict a separation of the capsule from the sheath by contacting the engaged portion in an opposition state in which the first surface faces the engaged portion,
- the capsule is rotatable about the longitudinal axis in response to a rotational force about the longitudinal axis from the sheath when the first surface is in the opposition state, and
- the arm member is rotatably connected to the operation wire such that the arm member is rotatable with respect to the operation wire.

15. The clip unit according to claim 14, wherein the engaging portion includes a plurality of ribs that protrude in a radial direction and are configured to engage the engaged portion when the sheath is rotated about the longitudinal axis to transmit the rotational force from the sheath to the capsule.

* * * * *